US010246492B2

(12) United States Patent
Tucker et al.

(10) Patent No.: US 10,246,492 B2
(45) Date of Patent: Apr. 2, 2019

(54) BOTULINUM ASSAY WITH SYNAPTOBREVIN SUBSTRATE MOIETY

(71) Applicant: BIOMADISON, INC, Del Mar, CA (US)

(72) Inventors: Ward C. Tucker, Monona, WI (US); Francis Mark Dunning, Madison, WI (US)

(73) Assignee: BIOMADISON, INC., Del Mar, CA (US)

( * ) Notice: Subject to any disclaimer, the term of this patent is extended or adjusted under 35 U.S.C. 154(b) by 209 days.

(21) Appl. No.: 14/941,452

(22) Filed: Nov. 13, 2015

(65) Prior Publication Data

US 2016/0069862 A1 Mar. 10, 2016

Related U.S. Application Data

(63) Continuation-in-part of application No. 13/502,357, filed as application No. PCT/US2010/052847 on Oct. 15, 2010, now Pat. No. 9,453,254.

(60) Provisional application No. 61/252,315, filed on Oct. 16, 2009.

(51) Int. Cl.

*C12N 9/52* (2006.01)
*C12Q 1/37* (2006.01)
*C07K 14/00* (2006.01)
*G01N 33/542* (2006.01)

(52) U.S. Cl.

CPC ................ *C07K 14/00* (2013.01); *C12N 9/52* (2013.01); *C12Q 1/37* (2013.01); *G01N 33/542* (2013.01); *G01N 2333/33* (2013.01)

(58) Field of Classification Search

None

See application file for complete search history.

(56) References Cited

U.S. PATENT DOCUMENTS

| | | | | |
|---|---|---|---|---|
| 5,981,200 | A | 11/1999 | Tsien et al. | |
| 7,094,888 | B2 | 8/2006 | Miesenbock et al. | |
| 2002/0076741 | A1 | 6/2002 | Tencza | |
| 2006/0134722 | A1 | 6/2006 | Chapman et al. | |
| 2007/0243565 | A1 | 10/2007 | Williams et al. | |
| 2012/0322092 | A1* | 12/2012 | Tucker | C12Q 1/37 435/23 |

FOREIGN PATENT DOCUMENTS

| | | |
|---|---|---|
| WO | 200026408 | 5/2000 |
| WO | 2005076785 | 8/2005 |
| WO | 2006107921 | 10/2006 |
| WO | 2009035476 | 3/2009 |

OTHER PUBLICATIONS

Gonzalo, S. et al., "SNAP-25 Is targeted to the Plasma Membrane through a Novel Membrane-binding Domain" The Journal of Biological Chemistry vol. 274, No. 30, Issue of Jul. 29, 1999, pp. 21313-21321.

Green, S. et al, "TestSmart—High Production Volume Chemicals: An Approach to Implementing Alternatives into Regulatory Toxicology" Toxicological Sciences 63, pp. 6-14 (2001) Copyright © 2001 by the Society of Toxicology.

Miyawaki et al., Fluorescent indicators for Ca2+ based on green fluorescent proteins and calmodulin, Letters to Nature, vol. 388, Aug. 1997, pp. 882-887.

Capkova et al., Investigations into Small Molecule Non-Peptidic Inhibitors of the Botulinum Neurotoxins, National Institutes of Health, Oct. 2009, vol. 54 (5), pp. 575-582.

Dong et al., Using fluorescent sensors to detect botulinum neurotoxin activity in vitro and in living cells, PNAS, Oct. 12, 2004, vol. 101, No. 41, pp. 14701-14706.

Fang et al., A yeast assay probes the interaction between botulinum neurotoxin serotype B and its SNARE substrate, PNAS, May 2, 2006, vol. 103, No. 18, pp. 6958-6963.

IPEA/US, International Preliminary Report on Patentability for International Application No. PCT/US10/52847, dated Nov. 11, 2011, 18 pages.

ISA/US, International Search Report and Written Opinion for International Application No. PCT/US10/52847, dated Feb. 22, 2011, 12 pages.

Joseph C. Larsen, U.S. Army Botulinum Neurotoxin (BoNT) Medical Therapeutics Research Program: Past Accomplishments and Future Directions, Drug Development Research, 2009, vol. 70, pp. 266-278.

Perpetuo et al., Enzymatic Profiling of Tetanus and Botulinum Neurotoxins Based on Vesicle-Associated-Membrane Protein Derived Fluorogenic Subtrates, Protein & Peptide Letters, 2008, vol. 15, pp. 1100-1106.

Pires-Alves et al., Tandem Fluorescent Proteins as Enhanced FRET-based Substrates for Botulinum Neurotoxin Activity, National Institutes of Health, Mar. 15, 2009, vol. 53 (4), pp. 392-399.

Siddiqui et al., Determinants of Synaptobrevin Regulation in Membranes, Molecular Biology of the Cell, Jun. 2007, vol. 18, pp. 2037-2046.

Sikorra et al., Substrate Recognition Mechanism of VAMP/Synaptobrevin-cleaving Clostridial Neurotoxins, The Journal of Biological Chemistry, Jul. 25, 2008, vol. 283, No. 30, pp. 21145-21152.

* cited by examiner

*Primary Examiner* — Paul J Holland

(74) *Attorney, Agent, or Firm* — Fish IP Law, LLP

(57) ABSTRACT

Compositions and methods for analyzing intracellular BoNT protease activity, and especially BoNT/B, BoNT/G, BoNT/D, and/or BoNT/F protease activity are provided. Cells express at least two recombinant hybrid proteins each of which includes a fluorophore and a membrane anchoring peptide, and at least one of which includes a BoNT protease recognition and cleavage sequence positioned to release a fluorophore upon cleavage. Analysis is performed by monitoring fluorescence following exposure to a BoNT.

11 Claims, 7 Drawing Sheets

Specification includes a Sequence Listing.

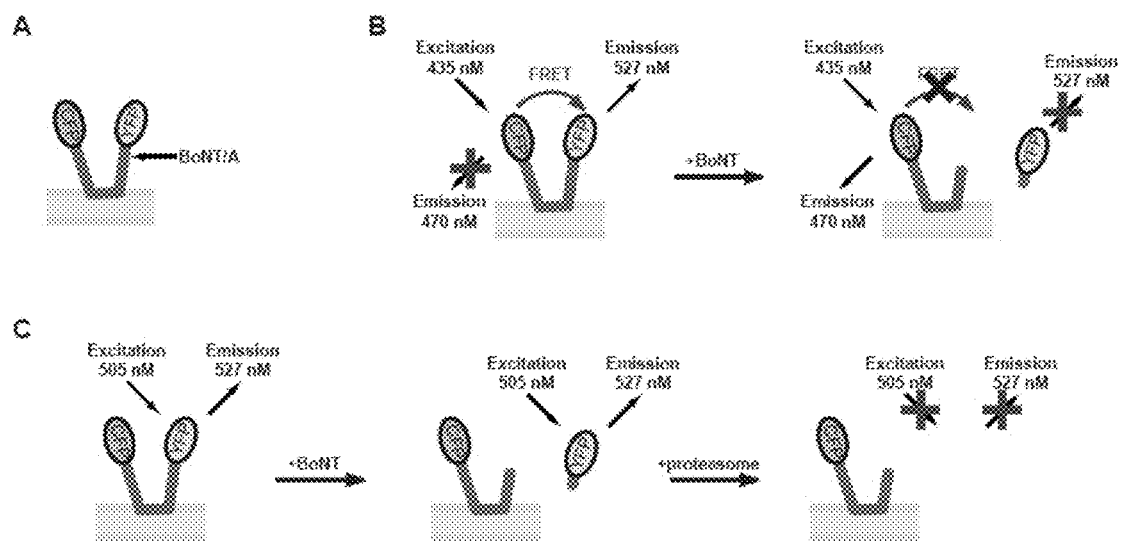
Prior Art Figure 1A
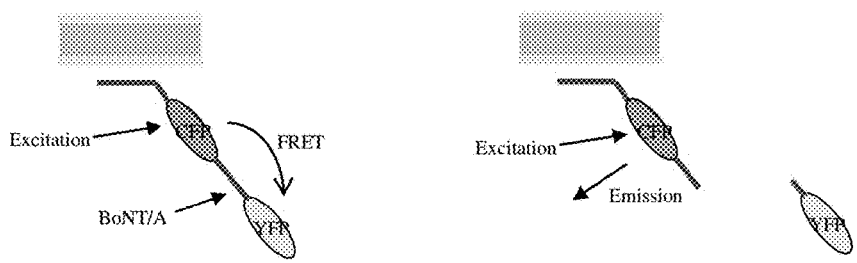
Prior Art Figure 1B

US 10,246,492 B2

BOTULINUM ASSAY WITH SYNAPTOBREVIN SUBSTRATE MOIETY

This application is a continuation in-part of U.S. application Ser. No. 13/502,357 filed on Apr. 16, 2012 entitled Resonance Energy Transfer Assay with Synaptobrevin Substrate Moiety and U.S. application Ser. No. 13/502,357 is a US national phase application based on International Application PCT/US10/52847 filed on Oct. 15, 2010 which claims priority to U.S. provisional application 61/252,315, filed on Oct. 16, 2009.

FIELD OF THE INVENTION

The field of the invention is Förster resonance energy transfer (FRET) assays for protease activity, especially protease assays for Botulinum neurotoxins BoNTs that cleave synaptobrevin.

BACKGROUND OF THE INVENTION

Botulinum neurotoxins (BoNTs) are extremely toxic proteins and can be classified into distinct subgroups based, inter alia, on peptide sequence and/or substrate specificity. All of the naturally occurring BoNTs (BoNT/A-G) are composed of a heavy chain that mediates toxin entry into a target cell and a light chain with zinc-dependent protease activity that hydrolyzes selected SNARE proteins that mediate fusion of neurotransmitter vesicles to the membrane that forms part of the synaptic cleft.

For example, the light chain of BoNT/A hydrolyzes with high specificity SNAP-25, which is required for vesicle-mediated exocytosis of acetylcholine into the synaptic cleft. Known assays for such hydrolytic activity include those described in our copending International application (WO 2009/035476), which is incorporated by reference herein. Here, a fluorophore and a quencher are covalently linked to the respective ends of a peptide sequence that includes, for example, the SNAP-25 sequence. Cleavage by BoNT/A (or other BoNTs with a substrate specificity towards SNAP-25) will result in physical separation of the cleavage products and so reduce fluorescence quenching, which can then be quantified. Among other choices, it is often preferred that such assay is performed as an in vitro solid-phase based assay.

While such assay is conceptually simple and can be used to readily determine BoNT/A, BoNT/C, or BoNT/E activity, such assay can not be simply modified to a cell-based assay for determination of BoNT/B, BoNT/D, BoNT/F, or BoNT/G activities by replacing the SNAP-25 motif with a SNARE domain as the SNARE domain includes a membrane spanning sub-domain that would place the N-terminal fluorophore into a vesicle lumen. In such case, only diffusion of the fluorescence signal would be observed as has been reported elsewhere (Dong et al. PNAS (2004), Vol. 101, No. 41, 14701-14706; or U.S. Pat. App. No. 2006/0134722).

Therefore, there is still a need for improved BoNT assays, and especially cell-based assays for BoNTs that cleave synaptobrevin.

SUMMARY OF THE INVENTION

The present invention is directed to various compositions and methods of analyzing BoNT protease activity, and especially BoNT/B, BoNT/G, BoNT/D, and/or BoNT/F protease activity in a cell-based system using fluorescence resonance energy transfer. Most preferably, the cells express one or more recombinant hybrid proteins together with at least one BoNT protease recognition and cleavage sequence, wherein the hybrid protein further comprises a transmembrane domain that is not cleavable by the BoNT protease and that directs the hybrid protein to an intracellular synaptic vesicle.

In one aspect of the inventive subject matter, a cell-based method of measuring protease activity of a BoNT protease, in which in one step a transfected cell is provided that produces (I) a hybrid protein having a structure of A-B-C-D or (II) two hybrid proteins having a structure of A-C-B and A-C-D, respectively, wherein A is a transmembrane domain that is not cleavable by the BoNT protease, B is a first fluorescent protein, C is a BoNT protease recognition and cleavage sequence, and D is a second fluorescent protein. IN another step, the transfected cell is contacted with a BoNT protease under conditions to allow the cell to take up the BoNT protease, and in yet another step, fluorescence is measured of at least one of the first and second fluorescent proteins in the transfected cell.

Most preferably, the transfected cell is a neuronal cell, a neuroendocrine tumor cell, a hybrid cell, or a stem cell. It is further generally preferred that A includes a transmembrane domain from synaptobrevin, synaptophysin, synapsin I, synapsin II, and/or synapsin III, and/or that C includes at least two of a BoNT/B, a BoNT/G, a BoNT/D, and a BoNT/F protease recognition and cleavage sequence. While not limiting to the inventive subject matter, it is further preferred that a peptide linker is disposed between one or more of A and C, A and B, C and B, and C and D, and that the linker has a length of equal or less than 12 amino acids. Additionally, it is contemplated that the transfected cell may be contacted with a putative or known BoNT inhibitor prior to contacting the transfected cell with the BoNT protease. In especially preferred aspects, the transfected cell produces two hybrid proteins.

In exemplary embodiments, the hybrid protein having the structure of A-B-C-D has a sequence according to SEQ ID NO:2, the hybrid protein having the structure of A-C-B has a sequence according to SEQ ID NO:4, and the hybrid protein having the structure of A-C-B has a sequence according to SEQ ID NO:6.

Therefore, and viewed from a different perspective, a recombinant nucleic acid includes a sequence that encodes (I) a hybrid protein having a structure of A-B-C-D or (II) two hybrid proteins having a structure of A-C-B and A-C-D, respectively, wherein A is a transmembrane domain that is not cleavable by the BoNT protease, B is a first fluorescent protein, C is a BoNT protease recognition and cleavage sequence, and D is a second fluorescent protein. Most preferably, A comprises a transmembrane domain from synaptobrevin, synaptophysin, synapsin I, synapsin II, and/ or synapsin III, and/or C comprises at least two of a BoNT/B, a BoNT/G, a BoNT/D, and a BoNT/F protease recognition and cleavage sequence. Where desired, at least one additional sequence may be provided that encodes a peptide linker that is disposed between at least one of A and C, A and B, C and B, and C and D, wherein the linker has a length of equal or less than 12 amino acids.

In especially preferred aspects, the recombinant nucleic acid encodes the two hybrid proteins. In exemplary nucleic acids, the hybrid protein having the structure of A-B-C-D is encoded by a sequence according to SEQ ID NO:1, the hybrid protein having the structure of A-C-B is encoded by a sequence according to SEQ ID NO:3, and the hybrid protein having the structure of A-C-B is encoded by a sequence according to SEQ ID NO:5.

Consequently, the inventors also contemplate a cell transfected with the nucleic acid presented herein, and it is generally preferred that the cell is stably transfected with the nucleic acid. Especially suitable cells include neuronal cells, neuroendocrine tumor cells, hybrid cells, and stem cells. Furthermore, it is typically preferred that the cell comprises a nucleic acid that encodes the two hybrid proteins having the structure of A-C-B and A-C-D.

Various objects, features, aspects and advantages of the present invention will become more apparent from the following detailed description of preferred embodiments of the invention.

BRIEF DESCRIPTION OF THE DRAWING

Prior Art FIGS. 1A-1B are known FRET assays for BoNT protease activity in which two fluorescent proteins are separated by a SNAP25 recognition and cleavage sequence.

FIG. 5A depicts the assay components prior to exposure to the BoNT. FIG. 5B depicts the assay components following exposure to the BoNT.

DETAILED DESCRIPTION

Figure 2A:
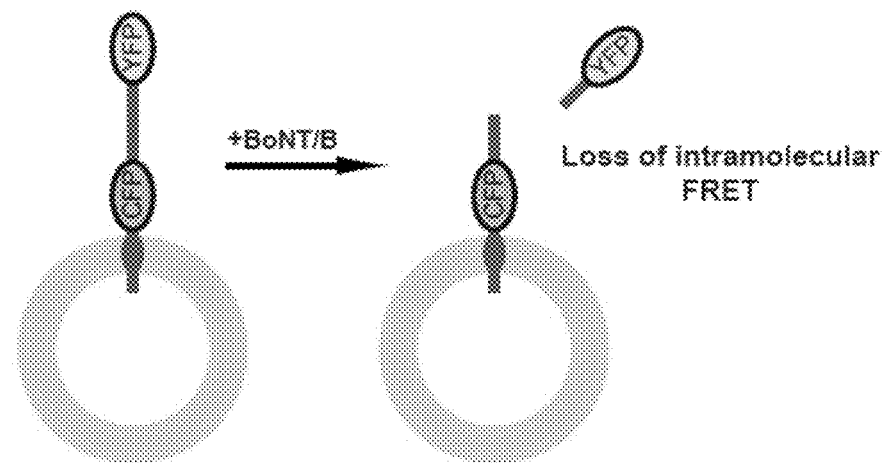
FIGS. 2B-2B are schematic illustrations for intramolecular (2A) and intermolecular (2B) FRET assays for BoNT protease activity according to the inventive subject matter.

According to the present invention a cell-based FRET assay for BoNT (and especially for BoNT/B, BoNT/D, BoNT/F, or BoNT/G) is provided in which a cell is transfected cell such that the cell produces (a) a single hybrid protein having a structure of A-B-C-D, or (b) two distinct hybrid proteins having a structure of A-C-B and A-C-D, respectively, in which A is a transmembrane domain, B is a first fluorescent protein, C is BoNT protease recognition and cleavage sequence, and D is a second fluorescent protein, where most typically, B and D allow for a FRET assay.

It should be appreciated that the hybrid protein(s) that are formed in the so transfected cells include a transmembrane domain. Therefore, these proteins are expected to locate to intracellular vesicles and to so present a vesicle-bound substrate. Upon exposure of the cells with BoNT, heavy chain-mediated endocytosis of the BoNT into the transfected cell is followed by presentation of the light chain on the outer surface of the vesicle, allowing the protease activity of the light chain to cleave the cleavage sequence of the hybrid protein(s), thus reducing FRET and providing a quantifiable signal. Therefore, it should be appreciated that the compositions and methods presented herein allow for a cell-based assay in which uptake, processing, and proteolytic activity can be monitored under conditions that closely resemble the natural conditions.

In contrast, as schematically depicted in Prior Art FIG. 1A, a BoNT/A test system with a hybrid protein is shown in A. The hybrid protein has first and second fluorescence proteins (CFP and YFP, respectively) covalently coupled to the respective termini of an intermediate peptide sequence that also includes a SNAP-25 sequence (which is the substrate for the BoNT/A light chain protease). Excitation of the CFP results in FRET-mediated fluorescence emission of YFP, thus creating a specific spectral fluorescence signature as schematically illustrated in B. Upon incubation with BoNT/A, the SNAP-25 sequence is hydrolyzed and YFP is released from the hybrid molecule (the remainder of which is still bound to a membrane or other solid phase) as depicted in C. Alternatively, or additionally, excitation and emission may be followed only using YFP, which when separated from the hybrid protein, will ultimately be processed in the proteasome complex. Similarly, as shown in Prior Art FIG. 1B, a hybrid protein has first and second fluorescence proteins (CFP and YFP, respectively) covalently coupled to the respective termini of an intermediate peptide sequence that also includes a SNAP-25 sequence. The hybrid protein is associated to the outside of the vesicle via the cysteine rich domain of the SNAP-25 sequence. Once more, upon cleavage of the SNAP-25 linker between the CFP and YFP, FRET is no longer available and fluorescence can be measured either as loss in FRET or ultimately loss in YFP as described above.

While such systems provide various advantages, it should be readily apparent that that where the SNAP-25 sequence is replaced by a synaptobrevin (VAMP), the presence of the transmembrane sub-domain in synaptobrevin will lead to physical separation of the CFP and YFP by the vesicle (or other) membrane, thus abolishing any FRET between the CFP and YFP as is shown in FIG. 9B of U.S. Pat. App. No. 2006/0134722.

To overcome these difficulties, the inventors now have prepared hybrid molecules suitable for intramolecular FRET in which one fluorescent protein (or other reporter) is positioned between the transmembrane sub-domain and the BoNT protease recognition and cleavage sequence, and wherein another fluorescent protein (or other reporter) is positioned following the BoNT protease recognition and cleavage sequence. Additionally, the inventors have also prepared pairs of hybrid molecules suitable for intermolecular FRET in which both hybrid molecules have a respective fluorescent protein coupled to respective sequences that include a transmembrane domain and a BoNT protease recognition and cleavage sequence.

As used herein, the term “transmembrane domain” refers to any molecular moiety that is capable of insertion into a plasma membrane in a manner such that at least a portion of the moiety extends into (and more typically across) the lipid bilayer. Thus, a moiety that only externally contacts (e.g., via ionic or electrostatic interaction) the outer surface of the plasma membrane is not considered a transmembrane domain under the definition provided herein. Thus, especially preferred transmembrane domains include hydrophobic polypeptide domains that extend into (and more typically across) the plasma membrane. Most typically, preferred transmembrane domains comprise a (typically recombinant) polypeptide. However, it should be recognized that various alternative elements (e.g., N-terminal palmitoylation) will also fall within the scope of the definition provided herein.

As also used herein, the term “BoNT recognition and cleavage sequence” refers to any molecular moiety that can be bound and cleaved by a BoNT protease. It is generally preferred that the BoNT recognition and cleavage sequence comprises a synaptobrevin polypeptide or portion thereof, which is typically a recombinant polypeptide.

In one especially preferred aspect of the inventive subject matter, contemplated recombinant nucleic acids may include a sequence that encodes (I) a hybrid protein having a structure of A-B-C-D or (II) at least one of two hybrid proteins having a structure of A-C-B and having a structure of A-C-D, respectively, where A is a transmembrane domain, B is a first fluorescent protein, C is a BoNT recognition and cleavage sequence, and D is a second fluorescent protein. Most preferably, where the sequence encodes two hybrid proteins, expression of the two hybrid proteins is under the control of respective promoters (typically, but not necessarily, having the same strength and same regulatory control mechanism).

Most typically, the transmembrane domain is selected such as to allow insertion of the recombinant protein(s) into the membrane of synaptic vesicles. Therefore, it is generally preferred that the transmembrane domain is the transmembrane domain of synaptobrevin, synaptophysin, synapsin I, synapsin II, and/or synapsin III, or any portion thereof that still confers anchoring of the recombinant protein into the membrane. However, in alternative aspects of the inventive subject matter, it is contemplated that various other transmembrane domains are also deemed suitable so long as such domains will anchor the recombinant protein to one or more intracellular membranes. There are numerous transmembrane domains known in the art, and all of those are deemed suitable for use herein. The person of ordinary skill in the art will readily be able to identify a domain as a transmembrane domain (e.g., via publication and description of the domain, or via computational domain analysis). Of course, suitable domains naturally occurring domains as well as mutated forms thereof (e.g., forms with one or more transitions, transversions, insertions, deletions, inversions, etc.). Moreover, additionally contemplated transmembrane domain may also be entirely synthetic and based on computational analysis.

Similarly, it should be appreciated that the transmembrane domain may also be replaced by another polypeptide moiety that allows at least temporary anchoring of the hybrid protein to a membrane such that the remainder of the hybrid protein is exposed to the cytosol. Anchoring may be mediated by various (typically non-covalent) interactions, including ionic, hydrophobic, and/or electrostatic interactions. Still further contemplated transmembrane domains also include non-protein transmembrane domains. For example, especially preferred alternative transmembrane domains will include those in which a hydrophobic group (e.g., sterol, hydrocarbon, etc.) is attached to the protein, and particularly a palmitoyl group. Such groups may be added intracellularly (e.g., via palmitoylation signal) or in vitro using various synthetic schemes.

It should further be appreciated that suitable transmembrane domains will preferably not include a BoNT protease cleavage site and/or a BoNT protease recognition site and thus only be acting as a transmembrane anchor for the recombinant protein. Therefore, suitable transmembrane domains may include full-length (or substantially full-length) synaptobrevin that has been sufficiently mutated to eliminate the cleavage site and/or recognition site. Alternatively, the synaptobrevin (or other transmembrane domain) may be truncated such that at least the cleavage site and/or recognition site is removed. Moreover, while the above is directed to single transmembrane domains, it should be appreciated that more than one transmembrane domains are also deemed appropriate (which are preferably coupled to each other via a spacer).

With respect to first and second fluorescent proteins it is generally contemplated that all known fluorescent proteins are suitable for use herein so long as such proteins can be used as specific and distinct signal generation moieties. However, it is particularly preferred that the signal generation moieties are fluorescent proteins that are suitable for FRET. For example, first and second fluorescent proteins can be Cyan Fluorescent Protein (CFP) and Yellow Fluorescent Protein (YFP) and their respective modifications, respectively. Of course, and as already noted above, the fluorescent proteins may be modified to include one or more specific characteristics (e.g., spectral) or be truncated to a specific size. Among other choices, contemplated fluorescent proteins include various blue fluorescent proteins (e.g., EBFP, EBFP2, Azurite, mKalama1), various cyan fluorescent proteins (e.g., ECFP, Cerulean, CyPet), various green fluorescent proteins (e.g., AcGFP1, ZsGreen1), and various yellow fluorescent protein derivatives (e.g., YFP, Citrine, Venus, YPet).

Similarly, it should be appreciated that the BoNT protease recognition and cleavage sequence may vary considerably, so long as such sequence is still recognized and hydrolyzed by a BoNT light chain. For example, the BoNT protease recognition and cleavage sequence may be of human, rat, or murine origin, may be present in oligo-multimeric form, and may be further specifically modified to facilitate or at least partially inhibit cleavage. Alternatively, the BoNT protease recognition and cleavage sequence may also be modified to allow identification of one or more specific BoNT subtypes (e.g., BoNT/B, D, F, and/or G, as well tetanus toxin) by preferential or exclusive cleavage. Of course, it should be recognized that all isoforms and mutants of BoNT protease recognition and cleavage sequences are also deemed suitable for use in conjunction with the teachings presented herein so long as such forms and mutants are also cleavable by one or more BoNT proteases. For example, suitable protease recognition and cleavage sequences include those from VAMP (Synaptobrevin) 1, 2, 3, 4, 5, 6, 7, or 8, and exemplary sequences are listed below where the recognition and cleavage domain is in regular type font, the transmembrane domain is in cursive type font, and where the actual cleavage positions for the respective BoNT proteases are underlined (QK: BoNT/F; KL: BoNT/D; QF: BoNT/B and TeTN; AA: BoNT/G):

Rat Vamp2 Protein Sequence (SEQ ID NO:7):

```
                                             SEQ ID NO: 7
MSATAATVPPAAPAGEGGPPAPPPNLTSNRRLQQTQAQVDEVVDIMRVNV
DKVLERDQKLSELDDRADALQAGASQFETSAAKLKRKYWWKNLKMMIILG
VICAIILIIIIVYFST
```

Mouse Vamp2 Protein Sequence (SEQ ID NO:8):

```
(SEQ ID NO: 8)
MSATAATVPPAAPAGEGGPPAPPPNLTSNRRLQQTQAQVDEVVDIMRVNV
DKVLERDQKLSELDDRADALQAGASQFETSAAKLKRKYWWKNLKMMIILG
VICAIILIIIIVYFST
```

Human Vamp2 Protein Sequence (SEQ ID NO:9):

```
                                            (SEQ ID NO: 9)
MSATAATAPPAAPAGEGGPPAPPPNLTSNRRLQQTQAQVDEVVDIMRVN
VDKVLERDQKLSELDDRADALQAGASQFETSAAKLKRKYWWKNLKMMII
LGVICAIILIIIIVYFST
```

Of course, it should be noted that the above sequences merely serve as examples for the sequences from which the transmembrane domain and the BoNT protease recognition and cleavage sequences can be obtained from. Thus, it is also noted that numerous alternative sequences other than synaptobrevin are also contemplated particularly if they can be cleaved by a naturally occurring or a synthetic or designer BoNT, including SNAP-25 and mutant forms thereof.

It should further be appreciated that one or more of the transmembrane domain, the first and second fluorescent proteins, and the BoNT protease recognition and cleavage domain may be truncated while retaining the respective function (i.e., transmembrane anchor, fluorescence, BoNT protease recognition and cleavage). Moreover, it should be appreciated that one or more amino acids in the above elements may be deleted or replaced by one or more other amino acids, typically in a conserved fashion.

Moreover, it is especially contemplated that the additional amino acids may be added as spacers between one or more of the transmembrane domain, the first and second fluorescent proteins, and the BoNT protease recognition and cleavage domain. Such spacers may be included to provide further steric flexibility, increase distance between the elements, etc. Typically, suitable spacers will have a length of between 1-100 amino acids, more typically between 2-50 amino acids, and most typically between 3-12 amino acids. Where the recombinant protein is used for FRET assays, shorter spacers are generally preferred. Still further, it is noted that additional domains may be provided to impart further desired functions. For example, suitable additional domains will include affinity tags for ease of isolation or antibody-based labeling, cell trafficking to direct the recombinant protein into a desired compartment, etc.

Figure 3A:
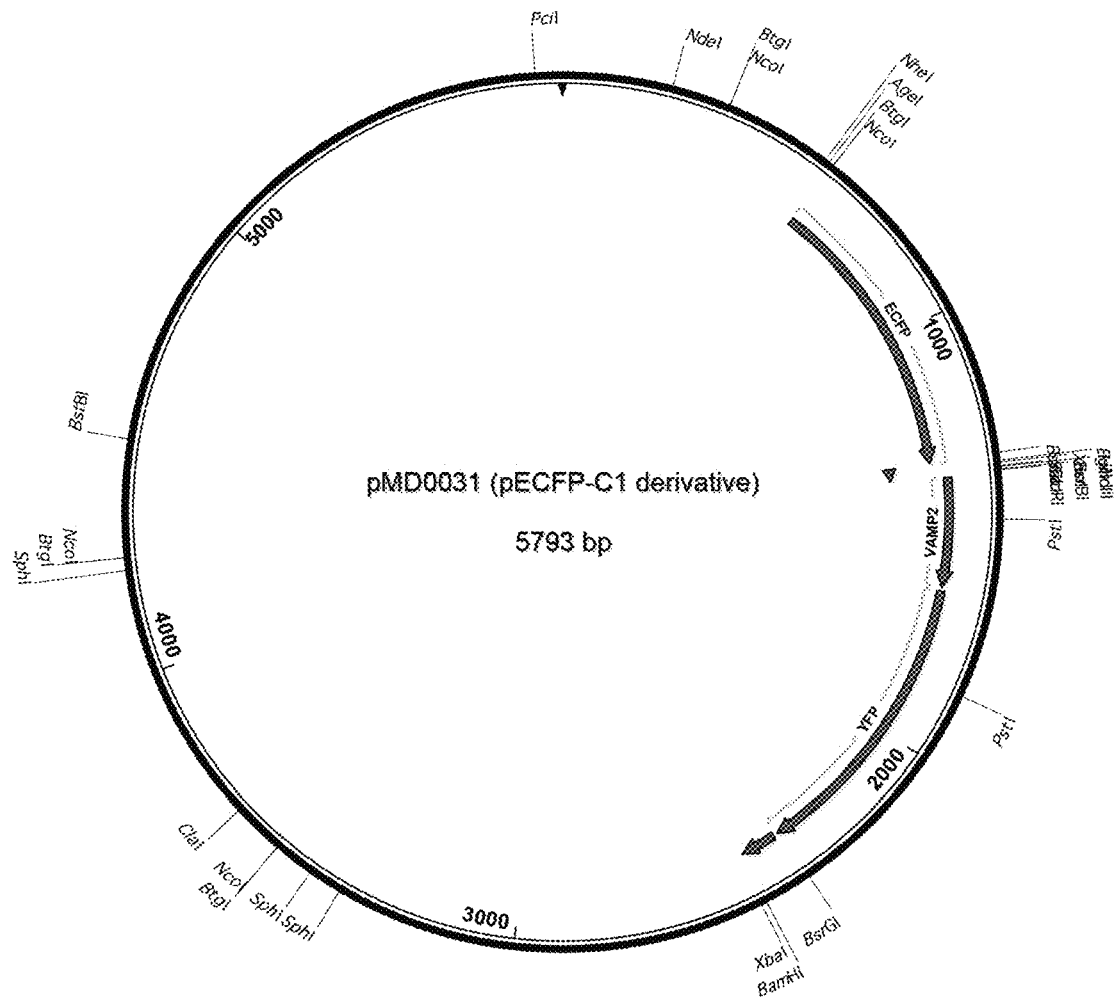
FIGS. 3A-3B are exemplary vector maps for recombinant intramolecular (3A) and intermolecular (3B) FRET constructs according to the inventive subject matter.
Figure 3B:
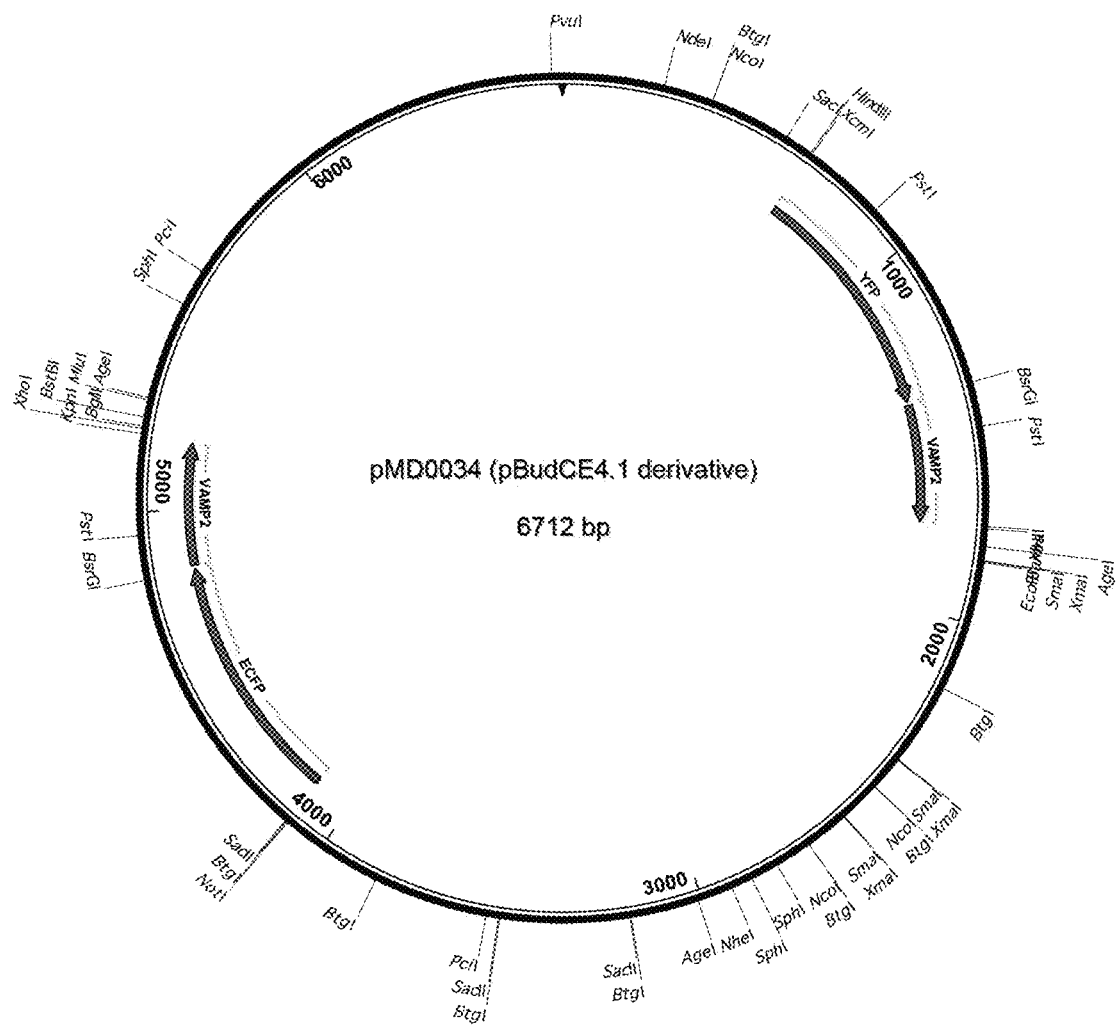

With respect to the transfected cells expressing the hybrid protein it is generally preferred that the cell is stably transfected. Nevertheless, transient transfection is also contemplated. There are numerous promoter structures known in the art, and all of those are generally deemed suitable for use herein. However, it is especially preferred that the expression is inducible from the promoter. In further contemplated aspects, expression may also be constitutively. FIG. 3A depicts an exemplary vector map for an expression construct of a hybrid protein having a structure of A-B-C-D, and FIG. 3B depicts an exemplary vector map for expression of two hybrid proteins having a structure of A-C-B and A-C-D, respectively.

Particularly preferred cells for transfection include neuronal cells (e.g., astrocytes, dendrocytes, glia cells, etc.) and stem cells (e.g., adult pluripotent, or adult germ line layer, or adult progenitor). However, numerous other non-neuronal cells, including human, rodent, insect cells, and even yeast and bacterial cells are also contemplated herein.

Consequently, the inventors contemplate a cell-based method of measuring protease activity of a BoNT protease in which in one step a transfected cell is provided that produces (I) a hybrid protein having a structure of A-B-C-D or (II) two hybrid proteins having a structure of A-C-B and A-C-D, respectively, wherein A is a transmembrane domain, B is a first fluorescent protein, C is a BoNT recognition and cleavage sequence, and D is a second fluorescent protein. In exemplary aspects of the inventive subject matter, the hybrid protein having a structure of A-B-C-D has a sequence according to SEQ ID NO:2, which is preferably encoded by a nucleic acid having sequence according to SEQ ID NO:1. Where the hybrid proteins have a structure of A-C-B and A-C-D, the protein sequences will preferably be as shown in SEQ ID NO:4 and SEQ ID NO:6, which are preferably encoded by a nucleic acid having sequence according to SEQ ID NO:3 and SEQ ID NO:5, respectively. Of course, and as already noted earlier, all mutant forms of the above sequences are also expressly contemplated herein, so long as such mutant forms retain the respective functions as noted above. In another step, the transfected cell is contacted with a BoNT protease under conditions to allow the cell to take up the BoNT protease, and in yet another step, fluorescence is measured from at least one of the first and second fluorescent proteins in the transfected cell.

Depending on the particular requirements and conditions, contemplated cell based assays may be performed as depicted in FIG. 2A in which the hybrid protein is a single polypeptide chain having an N-terminal transmembrane domain, followed by a CFP, which is in turn followed by a BoNT protease recognition and cleavage sequence, which is in turn followed by a (preferably terminal) YFP. Expression of the hybrid protein and subsequent translocation of the hybrid protein to the membrane of an intracellular vesicle will result in the presentation of the hybrid protein on the outside of the vesicle. The protease activity of BoNT/B will then intracellularly cleave the cleavage sequence, thus releasing the YFP from the hybrid protein. Consequently, quenching is reduced and fluorescence of the YFP is detectable in diffused form from the cell.

Figure 2B:
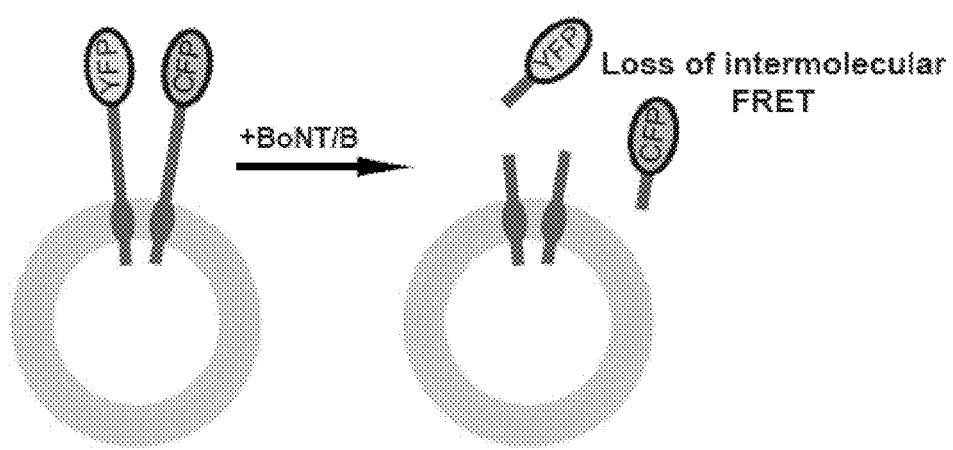
Figure 4A:
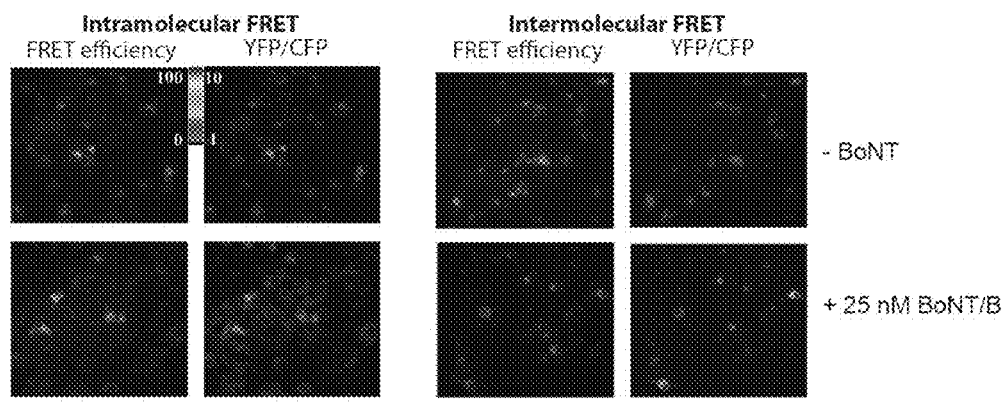
FIG. 4A depicts exemplary FRET results for intramolecular (left panel) and intermolecular (right panel) FRET analysis according to the inventive subject matter.
Figure 4B:
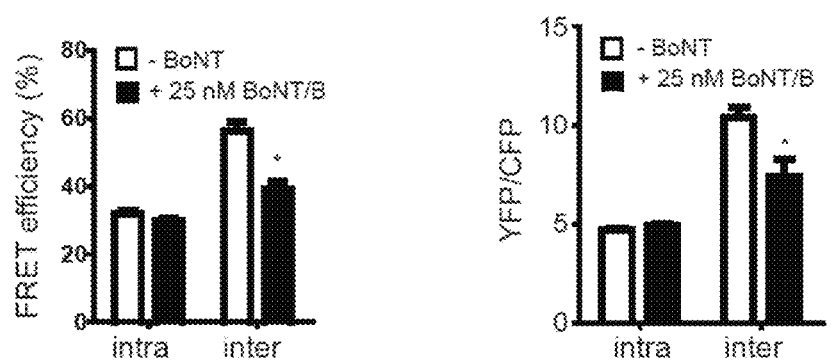
FIG. 4B is a graphic representation of the results from the experiments of FIG. 4A.

Alternatively, as shown in FIG. 2B, two separate hybrid proteins are formed in the cell, each having an N-terminal transmembrane domain, followed by a BoNT protease recognition and cleavage sequence, which is in turn followed by a (preferably terminal) YFP and CFP, respectively. Expression of the hybrid proteins and subsequent translocation of the hybrid proteins to the membrane of an intracellular vesicle will result in the presentation of the hybrid proteins on the outside of the vesicle. The protease activity of BoNT/B will then intracellularly cleave the cleavage sequences, thus releasing YFP and CFP from the hybrid protein. Consequently, quenching is reduced and fluorescence of the YFP and CFP is detectable in diffused form from the cell. Remarkably, the respective hybrid proteins co-locate on the vesicular membrane in such a manner as to allow for FRET. Exemplary results for such assays are depicted in the calculated fluorescence microphotographs of FIG. 4A and the corresponding bar graph representations of FIG. 4B. As can be readily taken from these figures, the FRET assay performed well in the intermolecular FRET assay and less satisfactorily in the intramolecular FRET assay. However, it is expected that routine experimentation will also provide satisfactory intramolecular FRET assay results.

In other embodiments, two separate hybrid proteins are formed in the cell, each having an N-terminal transmembrane domain. One of the hybrid proteins includes a fluorophore (for example, a peptide fluorophore derived from Green Fluorescent Protein) and a BoNT protease recognition sequence and cleavage sequence that intervenes between and is joined to both the transmembrane domain and the fluorophore. The second hybrid protein includes a second, different fluorophore (for example, a different peptide fluorophore derived from Green Fluorescent Protein) and a second, distinct non-cleavable intervening peptide sequence that does not include a BoNT cleavage sequence and is joined to both the transmembrane domain and the fluorophore. In some embodiments the second intervening peptide sequence can include a BoNT protease recognition sequence or a portion of a BoNT substrate protein, but does not include a BoNT cleavage sequence. In such a second hybrid protein the BoNT cleavage sequence can be partially or completely excised, modified by substitution with non-native amino acids, or be modified by post-translational modification (for example, treatment with reagents reactive with amino acid side chains). Peptide sequences associated with recognition by BoNTs and the sequences associated with cleavage by BoNTs can be found in the literature, for example in Sikorra et al., "Substrate Recognition Mechanism of VAMP/Synaptobrevin-cleaving Clostridial Neurotoxins" J. Biol. Chem. 283(30):21145-21152 (2008).

In such an embodiment the two hybrid proteins can associate and form all or part of a reporting construct complex. On exposure to a BoNT having specificity for the cleavage site sequence (for example, exposure of a synaptobrevin-based reporting construct complex to BoNT/B), only the fluorophore associated with the cleavage site-containing intervening sequence is released, whereas the fluorophore associated with the intervening sequence that does not include such a cleavage site is retained at the membrane. In preferred embodiments, the fluorophore associated with the cleavage site-containing intervening sequence is selected to be degradable by components of the cytosol, and release by a BoNT results in degradation of the released fluorophore relative to fluorophore associated with the membrane. In some embodiments, such a releasable fluorophore is selected to be more rapidly degraded (for example 1.5, 3, 10, 30, 100, or more than 100 times faster) in the cytosol than the fluorophore associated with the non-cleavable intervening sequence if found in the cytosol. For example, YFP can be associated with the cleavage site-containing intervening sequence and CFP can be associated with the intervening sequence that lacks a BoNT susceptible cleavage site. In some embodiments the fluorophores can be selected, oriented, and/or spaced such that meaningful (i.e. >5%) Foerster resonance energy transfer occurs between donor and acceptor fluorophore. In other embodiments, the fluorophores can be selected, oriented, and/or spaced such that no meaningful (i.e. less than or equal to 5%) Foerster resonance energy transfer occurs between the fluorophores.

In such embodiments, the fluorophore associated with the intervening sequence that lacks a BoNT cleavage sequence remains associated with a membrane following exposure to a BoNT. The emission from such a fluorophore can be utilized to normalize the emission observed from the fluorophore that is associated with the intervening sequence that includes a BoNT cleavage site, for example by calculating a ratio. Such normalization can be used to reduce assay variation resulting from differences in cell density, size, and/or distribution between different wells of test plate in a cell-based assay for BoNT activity.

Figure 5A:
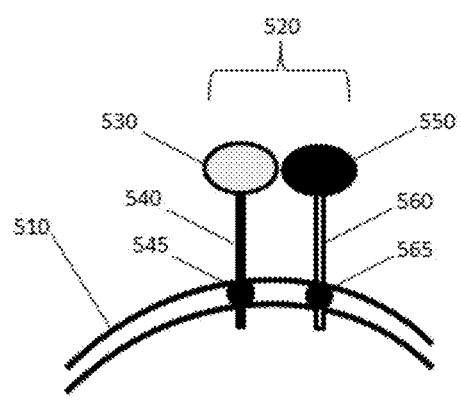
FIGS. 5A and 5B schematically depict an alternative embodiment of an intermolecular assay for BoNT activity.
Figure 5B:
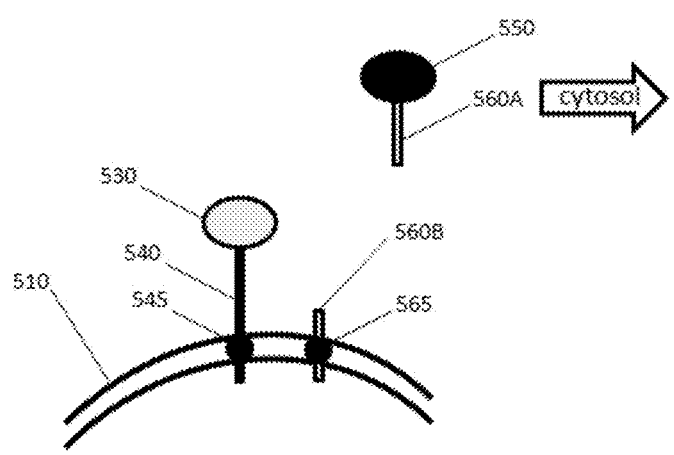

FIGS. 5A and 5B depict an embodiment of the inventive concept in which two hybrid proteins, one of which is not cleaved by a BoNT, are utilized. FIG. 5A shows a membrane 510 (for example, a vesicle membrane) that includes a reporting construct complex 520 prior to the introduction of or in the absence of a BoNT. The reporting construct complex includes at least two peptides. One peptide includes a first fluorophore 550 that is coupled to a transmembrane portion 565 by an intervening peptide 560. The intervening peptide 560 includes BoNT recognition and BoNT cleavage sequences, and hence is susceptible to cleavage by the proteolytic activity of a BoNT having specificity for those recognition and cleavage sequences. The other peptide includes a second fluorophore 530 that is coupled to a transmembrane portion 545 by an intervening peptide 540. The intervening peptide 540 is not cleavable by the BoNT that is capable of cleaving intervening peptide 560. In some embodiments the intervening peptide 540 is an analog of intervening peptide 560 (i.e. having 50%, 60%, 70%, 80%, 90%, 95%, or greater than 95% sequence identity) that does not include the BoNT cleavage site. For example, the intervening peptide 560 can include a synaptobrevin sequence than includes BoNT/B recognition and BoNT/B cleavage sequences, whereas intervening peptide 540 can include a synaptobrevin sequence that retains BoNT/B recognition sequences and does not include the BoNT/B cleavage sequence. The fluorophores 530 and 550 are distinguishable from one another (for example, by having different excitation/emission spectra), and can be selected and positioned (i.e. via spacing and/or orientation) to form a FRET pair, for example by selecting fluorophore 530 to have an emission spectrum that overlaps the excitation spectrum of fluorophore 550. In other embodiments the fluorophores can be selected and/or positioned such that significant FRET (i.e. >5%) does not occur.

FIG. 5B depicts the result of exposure of the reporting construct complex of FIG. 5A to a BoNT capable of cleaving the intervening peptide 560. As shown, such cleavage results in the cleavage of the intervening peptide into two fragments, 560A and 560B. Fragment 560B remains with the transmembrane sequence 565 while fragment 560 remains with the associated fluorophore 550, which is released into the cytoplasm. Since intervening peptide 540 is not cleaved, fluorophore 530 remains attached to the membrane following exposure to the BoNT. Release of fluorophore 550 can (in the case of reporting construct complexes exhibiting FRET) result in loss of FRET that is detectable by loss of emissions from the fluorophore. In addition, release into the cytosol can result in degradation of fluorophore 550, which can be detected by loss of emission from the fluorophore. Fluorophore 530, however, is not subject to cytosolic degradation, and as a result emission continues following BoNT treatment. In some embodiments an emission measurement from the fluorophore retained on the membrane following BoNT exposure is used to correct for variations in cell density, size, and/or distribution between wells of a test plate. This can be accomplished, for example, by calculating a ratio between the fluorescence emission measured from the fluorophore released by BoNT treatment and the fluorescence emission measured from the fluorophore retained following BoNT treatment.

EXAMPLES

Cloning of Intramolecular Construct

The intramolecular FRET construct, pMD0031 (FIG. 3A), was constructed in pEGFP-C1 (Clontech, Mountain View, Calif.). Three DNA fragments—an N-terminal fragment of rat Vamp2 from the start to amino acid 92, full length YFP without a stop codon, and a C-terminal fragment of rat Vamp2 from amino acid 93 to the stop—were amplified by polymerase chain reaction (PCR). An EcoRI restriction site was engineered onto the 5' end of the N-terminal Vamp2 fragment and a SerGlyGly (TCGGGAGGC) linker and the first 12 nucleotides of the YFP were engineered onto the 3' end. The YFP fragment had the last 13 nucleotides of the N-terminal Vamp2 fragment and the same SerGlyGly linker as the N-terminal Vamp2 fragment engineered onto the 5' end and a second SerGlyGly (AGCGGCGGT) linker and the first 9 nucleotides of the C-terminal Vamp2 fragment engineered onto the 3' end. The C-terminal Vamp2 fragment had the last 12 nucleotides of YFP without a stop and the same SerGlyGly linker as the YFP fragment engineered onto the 5' end and a BamHI restriction site engineered onto the 3' end.

These three fragments were then combined using splice overlap extension (SOE) PCR to create a single fragment consisting of an EcoRI restriction site, the N-terminal fragment of rat Vamp2 (amino acids 1-92), a SerGlyGly linker, YFP without a stop, a second SerGlyGly linker, the C-terminal fragment of rat Vamp2 (amino acids 93-stop), and an BamHI restriction site. This fragment and pECFP-C1 were then digested with EcoRI and BamHI, ligated together, and transformed into DH5α E. coli. The final construct insert was then fully sequenced.

Cloning of Intermolecular Construct

The intermolecular FRET construct, pMD0034 (FIG. 3B), was constructed in pBudCE4.1 (Invitrogen, Carlsbad, Calif.). The YFP rat Vamp2 fusion was generated by amplifying two fragments by PCR. The first fragment was YFP without a stop with an engineered HindIII restriction site on the 5' end and a SerGlyGly linker (AGTGGAGGC) and the first 9 nucleotides of rat Vamp2 engineered on the 3' end. The second fragment was full length rat Vamp2 with the last 9 nucleotides of YFP and the same SerGlyGly linker engineered onto the 5' end and an XbaI restriction site engineered onto the 3' end. These two fragments were then combined using SOE PCR to create a YFP, SerGlyGly linker, full length Vamp2 fragment. The fragment and pBudCE4.1 was then digested with HindIII and XbaI, ligated together, and transformed into DH5 α E. coli. The CFP rat Vamp2 fusion was created similarly but contained a CFP without a stop, a NotI restriction site on the 5' end, and a KpnI site on the 3' end. The final construct was then fully sequenced.

Cell Culture and FRET Assay

Analysis of FRET efficiency, YFP/CFP fluorescence ratios, and BoNT/B sensitivities of the BoNT/B reporters was performed in cells in vitro. More specifically, Neuro2A cells were grown in a 96-well plate to 70% confluency (~2000 cells/well) and transiently transfected using Lipofectamine 2000 (Invitrogen), with the intra- or intermolecular BoNT/B reporters. After 24 h, cells were incubated in the presence or absence of 25 nM BoNT/B at 37° C. for 72 h in 100 μl of phenol red-free MEM medium.

Semi-automated FRET or total YFP and CFP fluorescence measurements were performed using a Nikon TE2000-U fluorescent microscope with 200× magnification and Nikon NIS Elements 3.4 software. For FRET measurements, coefficients -A and -B (acceptor and donor) were calculated at 0.03 and 0.73 respectively, using a specific bleed-through method. FIG. 4A depicts randomly selected fields pseudo-colored for FRET efficiency or the YFP/CFP fluorescence ratio. YFP/CFP ratios were calculated from emissions collected upon direct excitement of each fluorophore. As can be seen from the graphic representation in FIG. 4B, the intermolecular BoNT/B reporter approach was significantly more sensitive for detection of BoNT/B in living cells. 30 randomly selected cells per condition were analyzed for FRET efficiency (FIG. 4A, left panels) or YFP/CFP fluorescence ratios (FIG. 4A, right panels) in the presence or absence of 25 nM BoNT/B. Indeed, such results were entirely unexpected as effective intermolecular FRET not only required balanced expression of the two fluorescent proteins, but also co-location of the recombinant proteins in corresponding quantities. The average signal from the 30 cells from 5 microscopic fields on 3 different wells is shown. Cells exhibiting over-saturated fluorescence were excluded.

Thus, specific embodiments and applications of BoNT assays have been disclosed. It should be apparent, however, to those skilled in the art that many more modifications besides those already described are possible without departing from the inventive concepts herein. The inventive subject matter, therefore, is not to be restricted except in the spirit of the appended claims.

SEQUENCE LISTING

```
<110>  BioMadison, Inc.

<120>  Botulinum Assay with Synaptobrevin Substrate Moiety

<130>  102320.0006US2

<160>  9

<170>  PatentIn version 3.4

<210>  1

<211>  1839

<212>  DNA

<213>  Artificial

<220>

<223>  Recombinant coding sequence for pMD0031

<220>

<221>  misc_feature

<222>  (1)..(717)

<223>  Enhanced Cyan Fluorescent Protein

<220>

<221>  misc_feature

<222>  (718)..(753)
```

SEQUENCE LISTING

<223> Linker

<220>

<221> misc_feature

<222> (754)..(1017)

<223> N-terminal portion of VAMP2 including all cleavage sites and no transmembrane domain

<220>

<221> misc_feature

<222> (1018)..(1026)

<223> SGG Linker

<220>

<221> misc_feature

<222> (1027)..(1743)

<223> Yellow Fluorescent Protein

<220>
<221> misc_feature

<222> (1744)..(1752)

<223> SGG Linker

<220>

<221> misc_feature

<222> (1753)..(1839)

<223> C-terminal portion of VAMP2 including transmembrane domain and no cleavage sites

<400> 1

```
atggtgagca agggcgagga gctgttcacc ggggtggtgc ccatcctggt cgagctggac    60
ggcgacgtaa acggccacaa gttcagcgtg tccggcgagg gcgagggcga tgccacctac   120
ggcaagctga ccctgaagtt catctgcacc accggcaagc tgcccgtgcc ctggcccacc   180
ctcgtgacca ccctgacctg gggcgtgcag tgcttcagcc gctaccccga ccacatgaag   240
cagcacgact tcttcaagtc cgccatgccc gaaggctacg tccaggagcg caccatcttc   300
ttcaaggacg acggcaacta caagacccgc gccgaggtga agttcgaggg cgacaccctg   360
gtgaaccgca tcgagctgaa gggcatcgac ttcaaggagg acggcaacat cctgggcac    420
aagctggagt acaactacat cagccacaac gtctatatca ccgccgacaa gcagaagaac   480
ggcatcaagg ccaacttcaa gatccgccac aacatcgagg acggcagcgt gcagctcgcc   540
gaccactacc agcagaacac ccccatcggc gacggccccg tgctgctgcc cgacaaccac   600
tacctgagca cccagtccgc cctgagcaaa gaccccaacg agaagcgcga tcacatggtc   660
ctgctggagt tcgtgaccgc cgccgggatc actctcggca tggacgagct gtacaagtcc   720
ggactcagat ctcgagctca agcttcgaat tctatgtcgg ctaccgctgc accgtcccg    780
cctgccgccc cggccggcga gggtggcccc cctgcacctc ctccaaatct taccagtaac   840
aggagactgc agcagaccca ggcccaggtg gatgaggtgg tggacatcat gagggtgaat   900
gtggacaagg tcctggagcg ggaccagaag ctatcggaac tggatgatcg cgcagatgcc   960
```

```
ctccaggcag gggcctccca gtttgaaaca agtgcagcca agctcaagcg caaatactcg  1020
ggaggcatgg tgagcaaggg cgaggagctg ttcaccgggg tggtgcccat cctggtcgag  1080
ctggacggcg acgtaaacgg ccacaagttc agcgtgtccg gcgagggcga gggcgatgcc  1140
acctacggca agctgaccct gaagttcatc tgcaccaccg gcaagctgcc cgtgccctgg  1200
cccaccctcg tgaccacctt cggctacggc ctgcagtgct tcgcccgcta ccccgaccac  1260
atgaagcagc acgacttctt caagtccgcc atgcccgaag ctacgtcca ggagcgcacc  1320 atcttcttca aggacgacgg caactacaag cccgcgccg aggtgaagtt cgagggcgac  1380
accctggtga accgcatcga gctgaagggc atcgacttca aggaggacgg caacatcctg  1440
gggcacaagc tggagtacaa ctacaacagc cacaacgtct atatcatggc cgacaagcag  1500
aagaacggca tcaaggtgaa cttcaagatc cgccacaaca tcgaggacgg cagcgtgcag  1560
ctcgccgacc actaccagca gaacacccccc atcggcgacg gccccgtgct gctgcccgac  1620
aaccactacc tgagctacca gtccgccctg agcaaagacc ccaacgagaa gcgcgatcac  1680
atggtcctgc tggagttcgt gaccgccgcc gggatcactc tcggcatgga cgagctgtac  1740
aagagcggcg gttggtggaa aaacctcaag atgatgatca tcttgggagt gatttgcgcc  1800
atcatcctca tcatcatcat cgtttacttc agcacttaa                          1839
```

```
<210>   2

<211>   612

<212>   PRT

<213>   Artificial

<220>

<223>   Recombinant protein encoded by pMD0031

<220>

<221>   MISC_FEATURE

<222>   (1)..(239)

<223>   Enhanced Cyan Fluorescent Protein

<220>

<221>   MISC_FEATURE

<222>   (240)..(251)

<223>   Linker

<220>

<221>   MISC_FEATURE

<222>   (252)..(339)

<223>   N-terminal portion of VAMP2 including all cleavage sites and no
        transmembrane domain

<220>

<221>   MISC_FEATURE

<222>   (340)..(342)

<223>   SGG Linker

<220>
```

SEQUENCE LISTING

<221> MISC_FEATURE

<222> (343)..(581)

<223> Yellow Fluorescent Protein

<220>

<221> MISC_FEATURE

<222> (582)..(584)

<223> SGG Linker

<220>

<221> MISC_FEATURE

<222> (585)..(612)

<223> C-terminal portion of VAMP2 including transmembrane domain and no cleavage sites

<400> 2

```
Met Val Ser Lys Gly Glu Glu Leu Phe Thr Gly Val Val Pro Ile Leu
1               5                   10                  15

Val Glu Leu Asp Gly Asp Val Asn Gly His Lys Phe Ser Val Ser Gly
            20                  25                  30

Glu Gly Glu Gly Asp Ala Thr Tyr Gly Lys Leu Thr Leu Lys Phe Ile
        35                  40                  45

Cys Thr Thr Gly Lys Leu Pro Val Pro Trp Pro Thr Leu Val Thr Thr
50                  55                  60

Leu Thr Trp Gly Val Gln Cys Phe Ser Arg Tyr Pro Asp His Met Lys
65                  70                  75                  80

Gln His Asp Phe Phe Lys Ser Ala Met Pro Glu Gly Tyr Val Gln Glu
                85                  90                  95

Arg Thr Ile Phe Phe Lys Asp Asp Gly Asn Tyr Lys Thr Arg Ala Glu
            100                 105                 110

Val Lys Phe Glu Gly Asp Thr Leu Val Asn Arg Ile Glu Leu Lys Gly
        115                 120                 125

Ile Asp Phe Lys Glu Asp Gly Asn Ile Leu Gly His Lys Leu Glu Tyr
130                 135                 140

Asn Tyr Ile Ser His Asn Val Tyr Ile Thr Ala Asp Lys Gln Lys Asn
145                 150                 155                 160

Gly Ile Lys Ala Asn Phe Lys Ile Arg His Asn Ile Glu Asp Gly Ser
                165                 170                 175

Val Gln Leu Ala Asp His Tyr Gln Gln Asn Thr Pro Ile Gly Asp Gly
            180                 185                 190

Pro Val Leu Leu Pro Asp Asn His Tyr Leu Ser Thr Gln Ser Ala Leu
        195                 200                 205

Ser Lys Asp Pro Asn Glu Lys Arg Asp His Met Val Leu Leu Glu Phe
210                 215                 220

Val Thr Ala Ala Gly Ile Thr Leu Gly Met Asp Glu Leu Tyr Lys Ser
225                 230                 235                 240

Gly Leu Arg Ser Arg Ala Gln Ala Ser Asn Ser Met Ser Ala Thr Ala
                245                 250                 255

Ala Thr Val Pro Pro Ala Ala Pro Ala Gly Glu Gly Gly Pro Pro Ala
            260                 265                 270
```

```
Pro Pro Pro Asn Leu Thr Ser Asn Arg Arg Leu Gln Gln Thr Gln Ala
        275                 280                 285

Gln Val Asp Glu Val Val Asp Ile Met Arg Val Asn Val Asp Lys Val
    290                 295                 300

Leu Glu Arg Asp Gln Lys Leu Ser Glu Leu Asp Asp Arg Ala Asp Ala
305                 310                 315                 320

Leu Gln Ala Gly Ala Ser Gln Phe Glu Thr Ser Ala Ala Lys Leu Lys
                325                 330                 335

Arg Lys Tyr Ser Gly Gly Met Val Ser Lys Gly Glu Glu Leu Phe Thr
            340                 345                 350

Gly Val Val Pro Ile Leu Val Glu Leu Asp Gly Asp Val Asn Gly His
        355                 360                 365

Lys Phe Ser Val Ser Gly Glu Gly Glu Gly Asp Ala Thr Tyr Gly Lys
    370                 375                 380

Leu Thr Leu Lys Phe Ile Cys Thr Thr Gly Lys Leu Pro Val Pro Trp
385                 390                 395                 400

Pro Thr Leu Val Thr Thr Phe Gly Tyr Gly Leu Gln Cys Phe Ala Arg
                405                 410                 415

Tyr Pro Asp His Met Lys Gln His Asp Phe Phe Lys Ser Ala Met Pro
            420                 425                 430

Glu Gly Tyr Val Gln Glu Arg Thr Ile Phe Phe Lys Asp Asp Gly Asn
        435                 440                 445

Tyr Lys Thr Arg Ala Glu Val Lys Phe Glu Gly Asp Thr Leu Val Asn
    450                 455                 460

Arg Ile Glu Leu Lys Gly Ile Asp Phe Lys Glu Asp Gly Asn Ile Leu
465                 470                 475                 480

Gly His Lys Leu Glu Tyr Asn Tyr Asn Ser His Asn Val Tyr Ile Met
                485                 490                 495

Ala Asp Lys Gln Lys Asn Gly Ile Lys Val Asn Phe Lys Ile Arg His
            500                 505                 510

Asn Ile Glu Asp Gly Ser Val Gln Leu Ala Asp His Tyr Gln Gln Asn
        515                 520                 525

Thr Pro Ile Gly Asp Gly Pro Val Leu Leu Pro Asp Asn His Tyr Leu
    530                 535                 540

Ser Tyr Gln Ser Ala Leu Ser Lys Asp Pro Asn Glu Lys Arg Asp His
545                 550                 555                 560

Met Val Leu Leu Glu Phe Val Thr Ala Ala Gly Ile Thr Leu Gly Met
                565                 570                 575

Asp Glu Leu Tyr Lys Ser Gly Gly Trp Trp Lys Asn Leu Lys Met Met
            580                 585                 590

Ile Ile Leu Gly Val Ile Cys Ala Ile Ile Leu Ile Ile Ile Ile Val
        595                 600                 605

Tyr Phe Ser Thr
    610

<210>   3

<211>   1077

<212>   DNA

<213>   Artificial

<220>

<223>   Recombinant coding sequence for intermolecular construct with YFP
```

SEQUENCE LISTING

<220>

<221> misc_feature

<222> (1)..(717)

<223> Yellow Fluorescence Protein

<220>

<221> misc_feature

<222> (718)..(726)

<223> SGG Linker

<220>

<221> misc_feature

<222> (727)..(1077)

<223> Full-length VAMP2 with transmembrane domain and cleavage sites

<400> 3

```
atggtgagca agggcgagga gctgttcacc ggggtggtgc ccatcctggt cgagctggac      60
ggcgacgtaa acggccacaa gttcagcgtg tccggcgagg gcgagggcga tgccacctac     120
ggcaagctga ccctgaagtt catctgcacc accggcaagc tgcccgtgcc ctggcccacc     180
ctcgtgacca ccttcggcta cggcctgcag tgcttcgccc gctacccga ccacatgaag      240
cagcacgact tcttcaagtc cgccatgccc gaaggctacg tccaggagcg caccatcttc     300
ttcaaggacg acggcaacta caagacccgc gccgaggtga agttcgaggg cgacaccctg     360
gtgaaccgca tcgagctgaa gggcatcgac ttcaaggagg acggcaacat cctggggcac     420
aagctggagt acaactacaa cagccacaac gtctatatca tggccgacaa gcagaagaac     480
ggcatcaagg tgaacttcaa gatccgccac aacatcgagg acggcagcgt gcagctcgcc     540
gaccactacc agcagaacac ccccatcggc gacggccccg tgctgctgcc cgacaaccac     600
tacctgagct accagtccgc cctgagcaaa gaccccaacg agaagcgcga tcacatggtc     660
ctgctggagt tcgtgaccgc cgccgggatc actctcggca tggacgagct gtacaagagt     720
ggaggcatgt cggctaccgc tgccaccgtc ccgcctgccg ccccggccgg cgagggtggc     780
cccctgcac  tcctccaaa tcttaccagt aacaggagac tgcagcagac ccaggcccag     840
gtggatgagg tggtggacat catgagggtg aatgtggaca aggtcctgga gcgagaccag     900
aagctatcgg aactggatga tcgcgcagat gccctccagg cagggcctc ccagtttgaa      960
acaagtgcag ccaagctcaa gcgcaaatac tggtggaaaa acctcaagat gatgatcatc    1020
ttgggagtga tttgcgccat catcctcatc atcatcatcg tttacttcag cacttaa       1077
```

<210> 4

<211> 358

<212> PRT

<213> Artificial

<220>

<223> Recombinant protein encoded by pMD0034 YFP

<220>

SEQUENCE LISTING

<221> MISC_FEATURE

<222> (1)..(239)

<223> Yellow Fluorescence Protein

<220>

<221> MISC_FEATURE

<222> (240)..(242)

<223> SGG Linker

<220>

<221> MISC_FEATURE

<222> (243)..(358)

<223> Full-length VAMP2 with transmembrane domain and cleavage sites

<400> 4

Met Val Ser Lys Gly Glu Glu Leu Phe Thr Gly Val Val Pro Ile Leu
1               5                   10                  15

Val Glu Leu Asp Gly Asp Val Asn Gly His Lys Phe Ser Val Ser Gly
            20                  25                  30

Glu Gly Glu Gly Asp Ala Thr Tyr Gly Lys Leu Thr Leu Lys Phe Ile
        35                  40                  45

Cys Thr Thr Gly Lys Leu Pro Val Pro Trp Pro Thr Leu Val Thr Thr
50                  55                  60

Phe Gly Tyr Gly Leu Gln Cys Phe Ala Arg Tyr Pro Asp His Met Lys
65                  70                  75                  80

Gln His Asp Phe Phe Lys Ser Ala Met Pro Glu Gly Tyr Val Gln Glu
                85                  90                  95

Arg Thr Ile Phe Phe Lys Asp Asp Gly Asn Tyr Lys Thr Arg Ala Glu
            100                 105                 110

Val Lys Phe Glu Gly Asp Thr Leu Val Asn Arg Ile Glu Leu Lys Gly
        115                 120                 125

Ile Asp Phe Lys Glu Asp Gly Asn Ile Leu Gly His Lys Leu Glu Tyr
130                 135                 140

Asn Tyr Asn Ser His Asn Val Tyr Ile Met Ala Asp Lys Gln Lys Asn
145                 150                 155                 160

Gly Ile Lys Val Asn Phe Lys Ile Arg His Asn Ile Glu Asp Gly Ser
                165                 170                 175

Val Gln Leu Ala Asp His Tyr Gln Gln Asn Thr Pro Ile Gly Asp Gly
            180                 185                 190

Pro Val Leu Leu Pro Asp Asn His Tyr Leu Ser Tyr Gln Ser Ala Leu
        195                 200                 205

Ser Lys Asp Pro Asn Glu Lys Arg Asp His Met Val Leu Leu Glu Phe
210                 215                 220

Val Thr Ala Ala Gly Ile Thr Leu Gly Met Asp Glu Leu Tyr Lys Ser
225                 230                 235                 240

Gly Gly Met Ser Ala Thr Ala Ala Thr Val Pro Pro Ala Ala Pro Ala
                245                 250                 255

Gly Glu Gly Gly Pro Pro Ala Pro Pro Pro Asn Leu Thr Ser Asn Arg
            260                 265                 270

Arg Leu Gln Gln Thr Gln Ala Gln Val Asp Glu Val Val Asp Ile Met
        275                 280                 285

SEQUENCE LISTING

```
Arg Val Asn Val Asp Lys Val Leu Glu Arg Asp Gln Lys Leu Ser Glu
    290                 295                 300
Leu Asp Asp Arg Ala Asp Ala Leu Gln Ala Gly Ala Ser Gln Phe Glu
305                 310                 315                 320
Thr Ser Ala Ala Lys Leu Lys Arg Lys Tyr Trp Trp Lys Asn Leu Lys
                325                 330                 335
Met Met Ile Ile Leu Gly Val Ile Cys Ala Ile Ile Leu Ile Ile Ile
            340                 345                 350
Ile Val Tyr Phe Ser Thr
            355
```

<210> 5

<211> 1077

<212> DNA

<213> Artificial

<220>

<223> Recombinant coding sequence for intermolecular construct with ECFP

<220>

<221> misc_feature

<222> (1)..(717)

<223> Enhanced Cyan Fluorescence Protein

<220>

<221> misc_feature

<222> (718)..(726)

<223> SGG Linker

<220>

<221> misc_feature

<222> (727)..(1077)

<223> Full-length VAMP2 with transmembrane domain and cleavage sites

<400> 5

```
atggtgagca agggcgagga gctgttcacc ggggtggtgc ccatcctggt cgagctggac     60
ggcgacgtaa acggccacaa gttcagcgtg tccggcgagg gcgagggcga tgccacctac    120
ggcaagctga ccctgaagtt catctgcacc accggcaagc tgcccgtgcc ctggcccacc    180
ctcgtgacca ccctgaccct gggcgtgcag tgcttcagcc gctaccccga ccacatgaag    240
cagcacgact tcttcaagtc cgccatgccc gaaggctacg tccaggagcg caccatcttc    300
ttcaaggacg acggcaacta caagacccgc gccgaggtga agttcgaggg cgacaccctg    360
gtgaaccgca tcgagctgaa gggcatcgac ttcaaggagg acggcaacat cctggggcac    420
aagctggagt acaactacat cagccacaac gtctatatca ccgccgacaa gcagaagaac    480
ggcatcaagg ccaacttcaa gatccgccac aacatcgagg acggcagcgt gcagctcgcc    540
gaccactacc agcagaacac ccccatcggc gacggccccg tgctgctgcc cgacaaccac    600
tacctgagca cccagtccgc cctgagcaaa gaccccaacg agaagcgcga tcacatggtc    660
```

```
ctgctggagt tcgtgaccgc cgccgggatc actctcggca tggacgagct gtacaagagt    720
ggaggcatgt cggctaccgc tgccaccgtc ccgcctgccg ccccggccgg cgagggtggc    780
ccccctgcac ctcctccaaa tcttaccagt aacaggagac tgcagcagac ccaggcccag    840
gtggatgagg tggtggacat catgagggtg aatgtggaca aggtcctgga gcgagaccag    900
aagctatcgg aactggatga tcgcgcagat gccctccagg caggggcctc ccagtttgaa    960
acaagtgcag ccaagctcaa gcgcaaatac tggtggaaaa acctcaagat gatgatcatc   1020
ttgggagtga tttgcgccat catcctcatc atcatcatcg tttacttcag cacttaa       1077
```

<210> 6
<211> 358
<212> PRT
<213> Artificial

<220>
<223> Recombinant protein encoded by pMD0034 ECFP

<220>
<221> MISC_FEATURE
<222> (1)..(239)
<223> Enhanced Cyan Fluorescence Protein <220>
<221> MISC_FEATURE
<222> (140)..(242)
<223> SGG Linker <220>
<221> MISC_FEATURE
<222> (243)..(358)
<223> Full-length VAMP2 with transmembrane domain and cleavage sites

<400> 6

```
Met Val Ser Lys Gly Glu Glu Leu Phe Thr Gly Val Val Pro Ile Leu
1               5                   10                  15

Val Glu Leu Asp Gly Asp Val Asn Gly His Lys Phe Ser Val Ser Gly
            20                  25                  30

Glu Gly Glu Gly Asp Ala Thr Tyr Gly Lys Leu Thr Leu Lys Phe Ile
        35                  40                  45

Cys Thr Thr Gly Lys Leu Pro Val Pro Trp Pro Thr Leu Val Thr Thr
    50                  55                  60

Leu Thr Trp Gly Val Gln Cys Phe Ser Arg Tyr Pro Asp His Met Lys
65                  70                  75                  80

Gln His Asp Phe Phe Lys Ser Ala Met Pro Glu Gly Tyr Val Gln Glu
                85                  90                  95

Arg Thr Ile Phe Phe Lys Asp Asp Gly Asn Tyr Lys Thr Arg Ala Glu
            100                 105                 110

Val Lys Phe Glu Gly Asp Thr Leu Val Asn Arg Ile Glu Leu Lys Gly
        115                 120                 125
```

| SEQUENCE LISTING |
|---|

```
Ile Asp Phe Lys Glu Asp Gly Asn Ile Leu Gly His Lys Leu Glu Tyr
    130                 135                 140

Asn Tyr Ile Ser His Asn Val Tyr Ile Thr Ala Asp Lys Gln Lys Asn
145                 150                 155                 160

Gly Ile Lys Ala Asn Phe Lys Ile Arg His Asn Ile Glu Asp Gly Ser
                165                 170                 175

Val Gln Leu Ala Asp His Tyr Gln Gln Asn Thr Pro Ile Gly Asp Gly
            180                 185                 190

Pro Val Leu Leu Pro Asp Asn His Tyr Leu Ser Thr Gln Ser Ala Leu
        195                 200                 205

Ser Lys Asp Pro Asn Glu Lys Arg Asp His Met Val Leu Leu Glu Phe
    210                 215                 220

Val Thr Ala Ala Gly Ile Thr Leu Gly Met Asp Glu Leu Tyr Lys Ser
225                 230                 235                 240

Gly Gly Met Ser Ala Thr Ala Ala Thr Val Pro Pro Ala Ala Pro Ala
                245                 250                 255

Gly Glu Gly Gly Pro Pro Ala Pro Pro Pro Asn Leu Thr Ser Asn Arg
            260                 265                 270

Arg Leu Gln Gln Thr Gln Ala Gln Val Asp Glu Val Val Asp Ile Met
        275                 280                 285

Arg Val Asn Val Asp Lys Val Leu Glu Arg Asp Gln Lys Leu Ser Glu
    290                 295                 300

Leu Asp Asp Arg Ala Asp Ala Leu Gln Ala Gly Ala Ser Gln Phe Glu
305                 310                 315                 320

Thr Ser Ala Ala Lys Leu Lys Arg Lys Tyr Trp Trp Lys Asn Leu Lys
                325                 330                 335

Met Met Ile Ile Leu Gly Val Ile Cys Ala Ile Ile Leu Ile Ile Ile
            340                 345                 350

Ile Val Tyr Phe Ser Thr
        355

<210>  7
<211>  116
<212>  PRT
<213>  Rattus norvegicus

<400>  7

Met Ser Ala Thr Ala Ala Thr Val Pro Pro Ala Ala Pro Ala Gly Glu
1               5                   10                  15

Gly Gly Pro Pro Ala Pro Pro Pro Asn Leu Thr Ser Asn Arg Arg Leu
                20                  25                  30

Gln Gln Thr Gln Ala Gln Val Asp Glu Val Val Asp Ile Met Arg Val
            35                  40                  45

Asn Val Asp Lys Val Leu Glu Arg Asp Gln Lys Leu Ser Glu Leu Asp
        50                  55                  60

Asp Arg Ala Asp Ala Leu Gln Ala Gly Ala Ser Gln Phe Glu Thr Ser
65                  70                  75                  80

Ala Ala Lys Leu Lys Arg Lys Tyr Trp Trp Lys Asn Leu Lys Met Met
                85                  90                  95

Ile Ile Leu Gly Val Ile Cys Ala Ile Ile Leu Ile Ile Ile Ile Val
            100                 105                 110
```

SEQUENCE LISTING

Tyr Phe Ser Thr
            115

<210>   8
<211>   116
<212>   PRT
<213>   Mus musculus
<400>   8

Met Ser Ala Thr Ala Ala Thr Val Pro Pro Ala Ala Pro Ala Gly Glu
1               5                   10                  15

Gly Gly Pro Pro Ala Pro Pro Asn Leu Thr Ser Asn Arg Arg Leu
                20              25                  30

Gln Gln Thr Gln Ala Gln Val Asp Glu Val Val Asp Ile Met Arg Val
            35                  40                  45

Asn Val Asp Lys Val Leu Glu Arg Asp Gln Lys Leu Ser Glu Leu Asp
    50                  55                  60

Asp Arg Ala Asp Ala Leu Gln Ala Gly Ala Ser Gln Phe Glu Thr Ser
65                  70                  75                  80

Ala Ala Lys Leu Lys Arg Lys Tyr Trp Trp Lys Asn Leu Lys Met Met
                85                  90                  95

Ile Ile Leu Gly Val Ile Cys Ala Ile Ile Leu Ile Ile Ile Val
                100                 105                 110

Tyr Phe Ser Thr
            115

<210>   9
<211>   116
<212>   PRT
<213>   Homo sapiens
<400>   9

Met Ser Ala Thr Ala Ala Thr Val Pro Pro Ala Ala Pro Ala Gly Glu
1               5                   10                  15

Gly Gly Pro Pro Ala Pro Pro Asn Leu Thr Ser Asn Arg Arg Leu
                20              25                  30

Gln Gln Thr Gln Ala Gln Val Asp Glu Val Val Asp Ile Met Arg Val
            35                  40                  45

Asn Val Asp Lys Val Leu Glu Arg Asp Gln Lys Leu Ser Glu Leu Asp
    50                  55                  60

Asp Arg Ala Asp Ala Leu Gln Ala Gly Ala Ser Gln Phe Glu Thr Ser
65                  70                  75                  80

Ala Ala Lys Leu Lys Arg Lys Tyr Trp Trp Lys Asn Leu Lys Met Met
                85                  90                  95

Ile Ile Leu Gly Val Ile Cys Ala Ile Ile Leu Ile Ile Ile Val
                100                 105                 110

Tyr Phe Ser Thr
            115

SEQUENCE LISTING

<160> NUMBER OF SEQ ID NOS: 9

<210> SEQ ID NO 1
<211> LENGTH: 1839
<212> TYPE: DNA
<213> ORGANISM: Artificial
<220> FEATURE:
<223> OTHER INFORMATION: Recombinant coding sequence for pMD0031
<220> FEATURE:
<221> NAME/KEY: misc_feature
<222> LOCATION: (1)..(717)
<223> OTHER INFORMATION: Enhanced Cyan Fluorescent Protein
<220> FEATURE:
<221> NAME/KEY: misc_feature
<222> LOCATION: (718)..(753)
<223> OTHER INFORMATION: Linker
<220> FEATURE:
<221> NAME/KEY: misc_feature
<222> LOCATION: (754)..(1017)
<223> OTHER INFORMATION: N-terminal portion of VAMP2 including all
      cleavage sites and no transmembrane domain
<220> FEATURE:
<221> NAME/KEY: misc_feature
<222> LOCATION: (1018)..(1026)
<223> OTHER INFORMATION: SGG Linker
<220> FEATURE:
<221> NAME/KEY: misc_feature
<222> LOCATION: (1027)..(1743)
<223> OTHER INFORMATION: Yellow Fluorescent Protein
<220> FEATURE:
<221> NAME/KEY: misc_feature
<222> LOCATION: (1744)..(1752)
<223> OTHER INFORMATION: SGG Linker
<220> FEATURE:
<221> NAME/KEY: misc_feature
<222> LOCATION: (1753)..(1839)
<223> OTHER INFORMATION: C-terminal portion of VAMP2 including
      transmembrane domain and no cleavage sites

<400> SEQUENCE: 1

```
atggtgagca agggcgagga gctgttcacc ggggtggtgc ccatcctggt cgagctggac      60
ggcgacgtaa acggccacaa gttcagcgtg tccggcgagg gcgagggcga tgccacctac     120
ggcaagctga ccctgaagtt catctgcacc accggcaagc tgcccgtgcc ctggcccacc     180
ctcgtgacca ccctgacctg gggcgtgcag tgcttcagcc gctaccccga ccacatgaag     240
cagcacgact cttcaagtc cgccatgccc gaaggctacg tccaggagcg caccatcttc     300
ttcaaggacg acggcaacta caagacccgc gccgaggtga agttcgaggg cgacaccctg     360
gtgaaccgca tcgagctgaa gggcatcgac ttcaaggagg acggcaacat cctggggcac     420
aagctggagt acaactacat cagccacaac gtctatatca ccgccgacaa gcagaagaac     480
ggcatcaagg ccaacttcaa gatccgccac aacatcgagg acggcagcgt gcagctcgcc     540
gaccactacc agcagaacac ccccatcggc gacggccccg tgctgctgcc cgacaaccac     600
tacctgagca cccagtccgc cctgagcaaa gaccccaacg agaagcgcga tcacatggtc     660
ctgctggagt tcgtgaccgc cgccgggatc actctcggca tggacgagct gtacaagtcc     720
ggactcagat tcgagctcca agcttcgaat tctatgtcgg ctaccgctgc accgtcccg     780
cctgccgccc cggccggcga gggtggcccc cctgcacctc ctccaaatct taccagtaac     840
aggagactgc agcagaccca ggcccaggtg gatgaggtgg tggacatcat gagggtgaat     900
gtggacaagg tcctggagcg ggaccagaag ctatcggaac tggatgatcg cgcagatgcc     960
ctccaggcag gggcctccca gtttgaaaca agtgcagcca agctcaagcg caaatactcg    1020
ggaggcatgt gagcaaggg cgaggagctg ttcaccgggg tggtgcccat cctggtcgag    1080
ctggacggcg acgtaaacgg ccacaagttc agcgtgtccg gcgagggcga gggcgatgcc    1140
```

```
acctacggca agctgaccct gaagttcatc tgcaccaccg gcaagctgcc cgtgccctgg    1200 cccacccteg tgaccacctt cggctacggc ctgcagtget tegeccgcta ccccgaccac    1260 atgaagcagc acgacttctt caagtccgcc atgcccgaag ctacgtcca ggagcgcacc     1320 atcttcttca aggacgacgg caactacaag acccgcgccg aggtgaagtt cgagggcgac    1380
accctggtga accgcatcga gctgaagggc atcgacttca aggaggacgg caacatcctg    1440
gggcacaagc tggagtacaa ctacaacagc cacaacgtct atatcatggc cgacaagcag    1500
aagaacggca tcaaggtgaa cttcaagatc cgccacaaca tcgaggacgg cagcgtgcag    1560
ctcgccgacc actaccagca gaacacccc atcggcacg ccccgtgct gctgcccgac       1620 aaccactacc tgagctacca gtccgccctg agcaaagacc ccaacgagaa gcgcgatcac    1680
atggtcctgc tggagttcgt gaccgccgcc gggatcactc tcggcatgga cgagctgtac    1740
aagagcggcg gttggtggaa aaacctcaag atgatgatca tcttgggagt gatttgcgcc    1800
atcatcctca tcatcatcat cgtttacttc agcacttaa                           1839
```

<210> SEQ ID NO 2
<211> LENGTH: 612
<212> TYPE: PRT
<213> ORGANISM: Artificial
<220> FEATURE:
<223> OTHER INFORMATION: Recombinant protein encoded by pMD0031
<220> FEATURE:
<221> NAME/KEY: MISC_FEATURE
<222> LOCATION: (1)..(239)
<223> OTHER INFORMATION: Enhanced Cyan Fluorescent Protein
<220> FEATURE:
<221> NAME/KEY: MISC_FEATURE
<222> LOCATION: (240)..(251)
<223> OTHER INFORMATION: Linker
<220> FEATURE:
<221> NAME/KEY: MISC_FEATURE
<222> LOCATION: (252)..(339)
<223> OTHER INFORMATION: N-terminal portion of VAMP2 including all
      cleavage sites and no transmembrane domain
<220> FEATURE:
<221> NAME/KEY: MISC_FEATURE
<222> LOCATION: (340)..(342)
<223> OTHER INFORMATION: SGG Linker
<220> FEATURE:
<221> NAME/KEY: MISC_FEATURE
<222> LOCATION: (343)..(581)
<223> OTHER INFORMATION: Yellow Fluorescent Protein
<220> FEATURE:
<221> NAME/KEY: MISC_FEATURE
<222> LOCATION: (582)..(584)
<223> OTHER INFORMATION: SGG Linker
<220> FEATURE:
<221> NAME/KEY: MISC_FEATURE
<222> LOCATION: (585)..(612)
<223> OTHER INFORMATION: C-terminal portion of VAMP2 including
      transmembrane domain and no cleavage sites

<400> SEQUENCE: 2

Met Val Ser Lys Gly Glu Glu Leu Phe Thr Gly Val Val Pro Ile Leu
1               5                   10                  15

Val Glu Leu Asp Gly Asp Val Asn Gly His Lys Phe Ser Val Ser Gly
                20                  25                  30

Glu Gly Glu Gly Asp Ala Thr Tyr Gly Lys Leu Thr Leu Lys Phe Ile
            35                  40                  45

Cys Thr Thr Gly Lys Leu Pro Val Pro Trp Pro Thr Leu Val Thr Thr
        50                  55                  60

Leu Thr Trp Gly Val Gln Cys Phe Ser Arg Tyr Pro Asp His Met Lys
65                  70                  75                  80

```
Gln His Asp Phe Phe Lys Ser Ala Met Pro Glu Gly Tyr Val Gln Glu
                85                  90                  95

Arg Thr Ile Phe Phe Lys Asp Asp Gly Asn Tyr Lys Thr Arg Ala Glu
            100                 105                 110

Val Lys Phe Glu Gly Asp Thr Leu Val Asn Arg Ile Glu Leu Lys Gly
        115                 120                 125

Ile Asp Phe Lys Glu Asp Gly Asn Ile Leu Gly His Lys Leu Glu Tyr
    130                 135                 140

Asn Tyr Ile Ser His Asn Val Tyr Ile Thr Ala Asp Lys Gln Lys Asn
145                 150                 155                 160

Gly Ile Lys Ala Asn Phe Lys Ile Arg His Asn Ile Glu Asp Gly Ser
                165                 170                 175

Val Gln Leu Ala Asp His Tyr Gln Gln Asn Thr Pro Ile Gly Asp Gly
            180                 185                 190

Pro Val Leu Leu Pro Asp Asn His Tyr Leu Ser Thr Gln Ser Ala Leu
        195                 200                 205

Ser Lys Asp Pro Asn Glu Lys Arg Asp His Met Val Leu Leu Glu Phe
    210                 215                 220

Val Thr Ala Ala Gly Ile Thr Leu Gly Met Asp Glu Leu Tyr Lys Ser
225                 230                 235                 240

Gly Leu Arg Ser Arg Ala Gln Ala Ser Asn Ser Met Ser Ala Thr Ala
                245                 250                 255

Ala Thr Val Pro Pro Ala Ala Pro Ala Gly Glu Gly Gly Pro Pro Ala
            260                 265                 270

Pro Pro Pro Asn Leu Thr Ser Asn Arg Arg Leu Gln Gln Thr Gln Ala
        275                 280                 285

Gln Val Asp Glu Val Val Asp Ile Met Arg Val Asn Val Asp Lys Val
    290                 295                 300

Leu Glu Arg Asp Gln Lys Leu Ser Glu Leu Asp Asp Arg Ala Asp Ala
305                 310                 315                 320

Leu Gln Ala Gly Ala Ser Gln Phe Glu Thr Ser Ala Ala Lys Leu Lys
                325                 330                 335

Arg Lys Tyr Ser Gly Gly Met Val Ser Lys Gly Glu Glu Leu Phe Thr
            340                 345                 350

Gly Val Val Pro Ile Leu Val Glu Leu Asp Gly Asp Val Asn Gly His
        355                 360                 365

Lys Phe Ser Val Ser Gly Glu Gly Glu Gly Asp Ala Thr Tyr Gly Lys
    370                 375                 380

Leu Thr Leu Lys Phe Ile Cys Thr Thr Gly Lys Leu Pro Val Pro Trp
385                 390                 395                 400

Pro Thr Leu Val Thr Thr Phe Gly Tyr Gly Leu Gln Cys Phe Ala Arg
                405                 410                 415

Tyr Pro Asp His Met Lys Gln His Asp Phe Phe Lys Ser Ala Met Pro
            420                 425                 430

Glu Gly Tyr Val Gln Glu Arg Thr Ile Phe Phe Lys Asp Asp Gly Asn
        435                 440                 445

Tyr Lys Thr Arg Ala Glu Val Lys Phe Glu Gly Asp Thr Leu Val Asn
    450                 455                 460

Arg Ile Glu Leu Lys Gly Ile Asp Phe Lys Glu Asp Gly Asn Ile Leu
465                 470                 475                 480

Gly His Lys Leu Glu Tyr Asn Tyr Asn Ser His Asn Val Tyr Ile Met
                485                 490                 495
```

```
Ala Asp Lys Gln Lys Asn Gly Ile Lys Val Asn Phe Lys Ile Arg His
            500                 505                 510

Asn Ile Glu Asp Gly Ser Val Gln Leu Ala Asp His Tyr Gln Gln Asn
            515                 520                 525

Thr Pro Ile Gly Asp Gly Pro Val Leu Leu Pro Asp Asn His Tyr Leu
            530                 535                 540

Ser Tyr Gln Ser Ala Leu Ser Lys Asp Pro Asn Glu Lys Arg Asp His
545                 550                 555                 560

Met Val Leu Leu Glu Phe Val Thr Ala Ala Gly Ile Thr Leu Gly Met
                565                 570                 575

Asp Glu Leu Tyr Lys Ser Gly Gly Trp Trp Lys Asn Leu Lys Met Met
            580                 585                 590

Ile Ile Leu Gly Val Ile Cys Ala Ile Ile Leu Ile Ile Ile Ile Val
            595                 600                 605

Tyr Phe Ser Thr
    610
```

<210> SEQ ID NO 3
<211> LENGTH: 1077
<212> TYPE: DNA
<213> ORGANISM: Artificial
<220> FEATURE:
<223> OTHER INFORMATION: Recombinant coding sequence for intermolecular construct with YFP
<220> FEATURE:
<221> NAME/KEY: misc_feature
<222> LOCATION: (1)..(717)
<223> OTHER INFORMATION: Yellow Fluorescence Protein
<220> FEATURE:
<221> NAME/KEY: misc_feature
<222> LOCATION: (718)..(726)
<223> OTHER INFORMATION: SGG Linker
<220> FEATURE:
<221> NAME/KEY: misc_feature
<222> LOCATION: (727)..(1077)
<223> OTHER INFORMATION: Full-length VAMP2 with transmembrane domain and cleavage sites

<400> SEQUENCE: 3

```
atggtgagca agggcgagga gctgttcacc ggggtggtgc ccatcctggt cgagctggac    60
ggcgacgtaa acggccacaa gttcagcgtg tccggcgagg gcgagggcga tgccacctac   120
ggcaagctga ccctgaagtt catctgcacc accggcaagc tgcccgtgcc ctggcccacc   180
ctcgtgacca cctccggcta cggcctgcag tgcttcgccc gctaccccga ccacatgaag   240
cagcacgact tcttcaagtc cgccatgccc gaaggctacg tccaggagcg caccatcttc   300
ttcaaggacg acggcaacta caagacccgc gccgaggtga agttcgaggg cgacaccctg   360
gtgaaccgca tcgagctgaa gggcatcgac ttcaaggagg acggcaacat cctgggccac   420
aagctggagt acaactacaa cagccacaac gtctatatca tggccgacaa gcagaagaac   480
ggcatcaagg tgaacttcaa gatccgccac aacatcgagg acggcagcgt gcagctcgcc   540
gaccactacc agcagaacac ccccatcggc gacggccccg tgctgctgcc cgacaaccac   600
tacctgagct accagtccgc cctgagcaaa gaccccaacg agaagcgcga tcacatggtc   660
ctgctggagt tcgtgaccgc cgccgggatc actctcggca tggacgagct gtacaagagt   720
ggaggcatgt cggctaccgc tgccaccgtc ccgcctgccg ccccggccgg cgagggtggc   780
ccccctgcac ctcctccaaa tcttaccagt aacaggagac tgcagcagac ccaggcccag   840
gtggatgagg tggtggacat catgagggtg aatgtggaca aggtcctgga gcagaccag    900
aagctatcgg aactggatga tcgcgcagat gccctccagg caggggcctc ccagtttgaa   960
```

```
acaagtgcag ccaagctcaa gcgcaaatac tggtggaaaa acctcaagat gatgatcatc    1020
ttgggagtga tttgcgccat catcctcatc atcatcatcg tttacttcag cacttaa       1077
```

<210> SEQ ID NO 4
<211> LENGTH: 358
<212> TYPE: PRT
<213> ORGANISM: Artificial
<220> FEATURE:
<223> OTHER INFORMATION: Recombinant protein encoded by pMD0034 YFP
<220> FEATURE:
<221> NAME/KEY: MISC_FEATURE
<222> LOCATION: (1)..(239)
<223> OTHER INFORMATION: Yellow Fluorescence Protein
<220> FEATURE:
<221> NAME/KEY: MISC_FEATURE
<222> LOCATION: (240)..(242)
<223> OTHER INFORMATION: SGG Linker
<220> FEATURE:
<221> NAME/KEY: MISC_FEATURE
<222> LOCATION: (243)..(358)
<223> OTHER INFORMATION: Full-length VAMP2 with transmembrane domain and
      cleavage sites

<400> SEQUENCE: 4

```
Met Val Ser Lys Gly Glu Glu Leu Phe Thr Gly Val Val Pro Ile Leu
1               5                   10                  15

Val Glu Leu Asp Gly Asp Val Asn Gly His Lys Phe Ser Val Ser Gly
            20                  25                  30

Glu Gly Glu Gly Asp Ala Thr Tyr Gly Lys Leu Thr Leu Lys Phe Ile
        35                  40                  45

Cys Thr Thr Gly Lys Leu Pro Val Pro Trp Pro Thr Leu Val Thr Thr
50                  55                  60

Phe Gly Tyr Gly Leu Gln Cys Phe Ala Arg Tyr Pro Asp His Met Lys
65                  70                  75                  80

Gln His Asp Phe Phe Lys Ser Ala Met Pro Glu Gly Tyr Val Gln Glu
                85                  90                  95

Arg Thr Ile Phe Phe Lys Asp Asp Gly Asn Tyr Lys Thr Arg Ala Glu
            100                 105                 110

Val Lys Phe Glu Gly Asp Thr Leu Val Asn Arg Ile Glu Leu Lys Gly
        115                 120                 125

Ile Asp Phe Lys Glu Asp Gly Asn Ile Leu Gly His Lys Leu Glu Tyr
130                 135                 140

Asn Tyr Asn Ser His Asn Val Tyr Ile Met Ala Asp Lys Gln Lys Asn
145                 150                 155                 160

Gly Ile Lys Val Asn Phe Lys Ile Arg His Asn Ile Glu Asp Gly Ser
                165                 170                 175

Val Gln Leu Ala Asp His Tyr Gln Gln Asn Thr Pro Ile Gly Asp Gly
            180                 185                 190

Pro Val Leu Leu Pro Asp Asn His Tyr Leu Ser Tyr Gln Ser Ala Leu
        195                 200                 205

Ser Lys Asp Pro Asn Glu Lys Arg Asp His Met Val Leu Leu Glu Phe
210                 215                 220

Val Thr Ala Ala Gly Ile Thr Leu Gly Met Asp Glu Leu Tyr Lys Ser
225                 230                 235                 240

Gly Gly Met Ser Ala Thr Ala Ala Thr Val Pro Pro Ala Ala Pro Ala
                245                 250                 255

Gly Glu Gly Gly Pro Pro Ala Pro Pro Pro Asn Leu Thr Ser Asn Arg
            260                 265                 270
```

```
Arg Leu Gln Gln Thr Gln Ala Gln Val Asp Glu Val Val Asp Ile Met
            275                 280                 285
Arg Val Asn Val Asp Lys Val Leu Glu Arg Asp Gln Lys Leu Ser Glu
        290                 295                 300
Leu Asp Asp Arg Ala Asp Ala Leu Gln Ala Gly Ala Ser Gln Phe Glu
305                 310                 315                 320
Thr Ser Ala Ala Lys Leu Lys Arg Lys Tyr Trp Trp Lys Asn Leu Lys
                325                 330                 335
Met Met Ile Ile Leu Gly Val Ile Cys Ala Ile Ile Leu Ile Ile Ile
            340                 345                 350
Ile Val Tyr Phe Ser Thr
            355

<210> SEQ ID NO 5
<211> LENGTH: 1077
<212> TYPE: DNA
<213> ORGANISM: Artificial
<220> FEATURE:
<223> OTHER INFORMATION: Recombinant coding sequence for intermolecular
      construct with ECFP
<220> FEATURE:
<221> NAME/KEY: misc_feature
<222> LOCATION: (1)..(717)
<223> OTHER INFORMATION: Enhanced Cyan Fluorescence Protein
<220> FEATURE:
<221> NAME/KEY: misc_feature
<222> LOCATION: (718)..(726)
<223> OTHER INFORMATION: SGG Linker
<220> FEATURE:
<221> NAME/KEY: misc_feature
<222> LOCATION: (727)..(1077)
<223> OTHER INFORMATION: Full-length VAMP2 with transmembrane domain and
      cleavage sites

<400> SEQUENCE: 5
atggtgagca agggcgagga gctgttcacc ggggtggtgc ccatcctggt cgagctggac      60
ggcgacgtaa acggccacaa gttcagcgtg tccggcgagg gcgagggcga tgccacctac     120
ggcaagctga ccctgaagtt catctgcacc accggcaagc tgcccgtgcc ctggcccacc     180
ctcgtgacca ccctgacctg gggcgtgcag tgcttcagcc gctaccccga ccacatgaag     240
cagcacgact tcttcaagtc cgccatgccc gaaggctacg tccaggagcg caccatcttc     300
ttcaaggacg acggcaacta caagacccgc gccgaggtga agttcgaggg cgacaccctg     360
gtgaaccgca tcgagctgaa gggcatcgac ttcaaggagg acggcaacat cctggggcac     420
aagctggagt acaactacat cagccacaac gtctatatca ccgccgacaa gcagaagaac     480
ggcatcaagg ccaacttcaa gatccgccac aacatcgagg acggcagcgt gcagctcgcc     540
gaccactacc agcagaacac ccccatcggc gacggccccg tgctgctgcc cgacaaccac     600
tacctgagca cccagtccgc cctgagcaaa gaccccaacg agaagcgcga tcacatggtc     660
ctgctggagt tcgtgaccgc cgccgggatc actctcggca tggacgagct gtacaagagt     720
ggaggcatgt cggctaccgc tgccaccgtc cgcctgccg ccccggccgg cgagggtggc     780
cccctgcac ctcctccaaa tcttaccagt aacaggagac tgcagcagac ccaggcccag     840
gtggatgagg tggtggacat catgagggtg aatgtggaca aggtcctgga gcgagaccag     900
aagctatcgg aactggatga tcgcgcagat gccctccagg cagggccctc ccagtttgaa     960
acaagtgcag ccaagctcaa gcgcaaatac tggtggaaaa acctcaagat gatgatcatc    1020
ttgggagtga tttgcgccat catcctcatc atcatcatcg tttacttcag cacttaa      1077
```

```
<210> SEQ ID NO 6
<211> LENGTH: 358
<212> TYPE: PRT
<213> ORGANISM: Artificial
<220> FEATURE:
<223> OTHER INFORMATION: Recombinant protein encoded by pMD0034 ECFP
<220> FEATURE:
<221> NAME/KEY: MISC_FEATURE
<222> LOCATION: (1)..(239)
<223> OTHER INFORMATION: Enhanced Cyan Fluorescence Protein
<220> FEATURE:
<221> NAME/KEY: MISC_FEATURE
<222> LOCATION: (140)..(242)
<223> OTHER INFORMATION: SGG Linker
<220> FEATURE:
<221> NAME/KEY: MISC_FEATURE
<222> LOCATION: (243)..(358)
<223> OTHER INFORMATION: Full-length VAMP2 with transmembrane domain and
      cleavage sites

<400> SEQUENCE: 6

Met Val Ser Lys Gly Glu Glu Leu Phe Thr Gly Val Val Pro Ile Leu
1               5                   10                  15

Val Glu Leu Asp Gly Asp Val Asn Gly His Lys Phe Ser Val Ser Gly
                20                  25                  30

Glu Gly Glu Gly Asp Ala Thr Tyr Gly Lys Leu Thr Leu Lys Phe Ile
            35                  40                  45

Cys Thr Thr Gly Lys Leu Pro Val Pro Trp Pro Thr Leu Val Thr Thr
50                  55                  60

Leu Thr Trp Gly Val Gln Cys Phe Ser Arg Tyr Pro Asp His Met Lys
65                  70                  75                  80

Gln His Asp Phe Phe Lys Ser Ala Met Pro Glu Gly Tyr Val Gln Glu
                85                  90                  95

Arg Thr Ile Phe Phe Lys Asp Asp Gly Asn Tyr Lys Thr Arg Ala Glu
            100                 105                 110

Val Lys Phe Glu Gly Asp Thr Leu Val Asn Arg Ile Glu Leu Lys Gly
        115                 120                 125

Ile Asp Phe Lys Glu Asp Gly Asn Ile Leu Gly His Lys Leu Glu Tyr
130                 135                 140

Asn Tyr Ile Ser His Asn Val Tyr Ile Thr Ala Asp Lys Gln Lys Asn
                145                 150                 155                 160

Gly Ile Lys Ala Asn Phe Lys Ile Arg His Asn Ile Glu Asp Gly Ser
            165                 170                 175

Val Gln Leu Ala Asp His Tyr Gln Gln Asn Thr Pro Ile Gly Asp Gly
        180                 185                 190

Pro Val Leu Leu Pro Asp Asn His Tyr Leu Ser Thr Gln Ser Ala Leu
    195                 200                 205

Ser Lys Asp Pro Asn Glu Lys Arg Asp His Met Val Leu Leu Glu Phe
210                 215                 220

Val Thr Ala Ala Gly Ile Thr Leu Gly Met Asp Glu Leu Tyr Lys Ser
225                 230                 235                 240

Gly Gly Met Ser Ala Thr Ala Ala Thr Val Pro Pro Ala Ala Pro Ala
                245                 250                 255

Gly Glu Gly Gly Pro Pro Ala Pro Pro Pro Asn Leu Thr Ser Asn Arg
            260                 265                 270

Arg Leu Gln Gln Thr Gln Ala Gln Val Asp Glu Val Val Asp Ile Met
        275                 280                 285

Arg Val Asn Val Asp Lys Val Leu Glu Arg Asp Gln Lys Leu Ser Glu
    290                 295                 300
```

```
Leu Asp Asp Arg Ala Asp Ala Leu Gln Ala Gly Ala Ser Gln Phe Glu
305                 310                 315                 320

Thr Ser Ala Ala Lys Leu Lys Arg Lys Tyr Trp Trp Lys Asn Leu Lys
                325                 330                 335

Met Met Ile Ile Leu Gly Val Ile Cys Ala Ile Ile Leu Ile Ile Ile
            340                 345                 350

Ile Val Tyr Phe Ser Thr
        355

<210> SEQ ID NO 7
<211> LENGTH: 116
<212> TYPE: PRT
<213> ORGANISM: Rattus norvegicus

<400> SEQUENCE: 7

Met Ser Ala Thr Ala Ala Thr Val Pro Pro Ala Ala Pro Ala Gly Glu
1               5                   10                  15

Gly Gly Pro Pro Ala Pro Pro Pro Asn Leu Thr Ser Asn Arg Arg Leu
            20                  25                  30

Gln Gln Thr Gln Ala Gln Val Asp Glu Val Val Asp Ile Met Arg Val
        35                  40                  45

Asn Val Asp Lys Val Leu Glu Arg Asp Gln Lys Leu Ser Glu Leu Asp
50                  55                  60

Asp Arg Ala Asp Ala Leu Gln Ala Gly Ala Ser Gln Phe Glu Thr Ser
65                  70                  75                  80

Ala Ala Lys Leu Lys Arg Lys Tyr Trp Trp Lys Asn Leu Lys Met Met
                85                  90                  95

Ile Ile Leu Gly Val Ile Cys Ala Ile Ile Leu Ile Ile Ile Ile Val
            100                 105                 110

Tyr Phe Ser Thr
            115

<210> SEQ ID NO 8
<211> LENGTH: 116
<212> TYPE: PRT
<213> ORGANISM: Mus musculus

<400> SEQUENCE: 8

Met Ser Ala Thr Ala Ala Thr Val Pro Pro Ala Ala Pro Ala Gly Glu
1               5                   10                  15

Gly Gly Pro Pro Ala Pro Pro Pro Asn Leu Thr Ser Asn Arg Arg Leu
            20                  25                  30

Gln Gln Thr Gln Ala Gln Val Asp Glu Val Val Asp Ile Met Arg Val
        35                  40                  45

Asn Val Asp Lys Val Leu Glu Arg Asp Gln Lys Leu Ser Glu Leu Asp
50                  55                  60

Asp Arg Ala Asp Ala Leu Gln Ala Gly Ala Ser Gln Phe Glu Thr Ser
65                  70                  75                  80

Ala Ala Lys Leu Lys Arg Lys Tyr Trp Trp Lys Asn Leu Lys Met Met
                85                  90                  95

Ile Ile Leu Gly Val Ile Cys Ala Ile Ile Leu Ile Ile Ile Ile Val
            100                 105                 110

Tyr Phe Ser Thr
            115

<210> SEQ ID NO 9
<211> LENGTH: 116
```

```
<212> TYPE: PRT
<213> ORGANISM: Homo sapiens

<400> SEQUENCE: 9

Met Ser Ala Thr Ala Ala Thr Ala Pro Pro Ala Ala Pro Ala Gly Glu
1               5                   10                  15

Gly Gly Pro Pro Ala Pro Pro Pro Asn Leu Thr Ser Asn Arg Arg Leu
            20                  25                  30

Gln Gln Thr Gln Ala Gln Val Asp Glu Val Val Asp Ile Met Arg Val
            35                  40                  45

Asn Val Asp Lys Val Leu Glu Arg Asp Gln Lys Leu Ser Glu Leu Asp
        50                  55                  60

Asp Arg Ala Asp Ala Leu Gln Ala Gly Ala Ser Gln Phe Glu Thr Ser
65                  70                  75                  80

Ala Ala Lys Leu Lys Arg Lys Tyr Trp Trp Lys Asn Leu Lys Met Met
                85                  90                  95

Ile Ile Leu Gly Val Ile Cys Ala Ile Ile Leu Ile Ile Ile Ile Val
            100                 105                 110

Tyr Phe Ser Thr
            115
```

What is claimed is:

1. A recombinant nucleic acid comprising:
a sequence that encodes a first hybrid proteins having a structure of A-C-B and a second hybrid protein having a structure of A-C' D;
wherein A is a transmembrane protein domain of synaptobrevin targeted to an intracellular vesicle membrane and is not cleavable by a Botulinum neurotoxin protease, B is a first fluorescent protein, C is a first linking domain comprising a Botulinum neurotoxin protease recognition sequence and a Botulinum neurotoxin protease cleavage sequence, C' is a second linking domain comprising an analog of C that includes the Botulinum neurotoxin protease recognition sequence but not the Botulinum neurotoxin protease cleavage sequence, and D is a second fluorescent protein selected to form a Förster resonance energy transfer (FRET) pair with the first fluorescent protein, wherein said transmembrane domain, said peptide spacer, and said BoNT protease recognition and cleavage sequence are selected to support FRET between said first fluorescent protein and said second fluorescent protein when said first hybrid protein and said second hybrid protein are collocated with a vesicle.

2. The recombinant nucleic acid of claim 1 wherein C comprises at least one of the group consisting of a Botulinum neurotoxin/B protease recognition and protease cleavage sequence, a Botulinum neurotoxin/G protease recognition and protease cleavage sequence, a Botulinum neurotoxin/D protease recognition and protease cleavage sequence, and a Botulinum neurotoxin/F protease recognition and protease cleavage sequence, and wherein C' comprises at least one of the group consisting of a Botulinum neurotoxin/B protease recognition sequence absent the corresponding protease cleavage sequence, a Botulinum neurotoxin/G protease recognition sequence absent the corresponding protease cleavage sequence, a Botulinum neurotoxin/D protease recognition sequence absent the corresponding protease cleavage sequence, and a Botulinum neurotoxin/F protease recognition sequence absent the corresponding protease cleavage sequence.

3. A transfected cell comprising:
a nucleic acid comprising a sequence that encodes a first hybrid protein having a structure of A-C-B and a second hybrid protein having a structure of A-C'-D;
wherein A is a transmembrane protein domain of synaptobrevin targeted to an intracellular vesicle membrane, and that is not cleavable by a Botulinum neurotoxin protease, B is a first fluorescent protein, C is a first linking region comprising a Botulinum neurotoxin protease recognition sequence and Botulinum neurotoxin protease cleavage sequence, C' is a second linking region comprising an analog of C that includes the Botulinum neurotoxin protease recognition sequence but not the Botulinum neurotoxin protease cleavage sequence, and D is a second fluorescent protein selected to form a FRET pair with the first fluorescent protein, wherein said transmembrane domain, said peptide space, and said BoNT protease recognition and cleavage sequence are selected to support FRET between said first fluorescent protein and said second fluorescent protein when said first hybrid protein and said second hybrid protein are collated with a vesicle.

4. The transfected cell of claim 3, wherein the cell is stably transfected with the nucleic acid.

5. The transfected cell of claim 3, wherein the cell is a cell selected from the group consisting of a neuronal cell, a neuroendocrine tumor cell, a hybrid cell, and a stem cell.

6. The transfected cell of claim 3, wherein the two hybrid proteins form at least a portion of a reporting construct complex, and wherein the first fluorescent protein and the second fluorescent protein demonstrate significant Förster resonance energy transfer within the reporting construct complex as compared to a reporting construct complex without said two hybrid proteins.

7. A cell-based method of measuring protease activity of a BoNT protease, comprising providing the transfected cell of claim 3;

contacting the transfected cell with a BoNT protease under conditions to take up the BoNT protease by the transfected cell; and measuring FRET in said transfected cell, thereby measuring protease activity of said BoNT protease.

8. The method of claim 7, wherein the transfected cell is a cell selected from the group consisting of a neuronal cell, a neuroendocrine tumor cell, a hybrid cell, and a stem cell.

9. The method of claim 7, further comprising a step of contacting the transfected cell with a putative BoNT inhibitor prior to contacting the transfected cell with the BoNT protease.

10. The recombinant nucleic acid of claim 1, wherein C and C' are derived from synaptobrevin.

11. The cell of claim 3, wherein C and C' are derived from synaptobrevin.

* * * * *